(12) United States Patent
Yanagawa

(10) Patent No.: US 12,006,458 B2
(45) Date of Patent: Jun. 11, 2024

(54) COMPLEX AND DETECTION DEVICE

(71) Applicant: Panasonic Intellectual Property Management Co., Ltd., Osaka (JP)

(72) Inventor: Hiroto Yanagawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 722 days.

(21) Appl. No.: 17/118,652

(22) Filed: Dec. 11, 2020

(65) Prior Publication Data

US 2021/0095198 A1    Apr. 1, 2021

Related U.S. Application Data

(63) Continuation of application No. PCT/JP2019/040065, filed on Oct. 10, 2019.

(30) Foreign Application Priority Data

Nov. 30, 2018 (JP) ................. 2018-225053

(51) Int. Cl.
C09K 11/59    (2006.01)
B82Y 15/00    (2011.01)
(Continued)

(52) U.S. Cl.
CPC .............. C09K 11/59 (2013.01); C09K 11/02 (2013.01); G01N 21/6428 (2013.01);
(Continued)

(58) Field of Classification Search
CPC ................. C09K 11/59; C09K 11/02
See application file for complete search history.

(56) References Cited

U.S. PATENT DOCUMENTS

2007/0292688 A1    12/2007    Bringley et al.
2010/0255462 A1    10/2010    Tsukada et al.
(Continued)

FOREIGN PATENT DOCUMENTS

JP    2004-083712    3/2004
JP    2009-504742    2/2009
(Continued)

OTHER PUBLICATIONS

International Search Report of PCT application No. PCT/JP2019/040065 dated Dec. 24, 2019.
(Continued)

*Primary Examiner* — C Melissa Koslow
(74) *Attorney, Agent, or Firm* — Rimon P.C.

(57) ABSTRACT

The present disclosure provides a complex having satisfactory dispersibility and stable luminescence characteristics. A complex of the present disclosure includes: a first substance having a property of specifically binding to a target substance; a quantum dot that contains silicon as a main component and that is negatively charged on a surface; and a linker substance that contains a compound represented by general formula (1) below and that covers the surface of the quantum dot, where the first substance has been immobilized on the surface of the quantum dot through the linker substance:

$$X\text{—}L\text{—}Si\text{—}(R_1)(R_2)(OR_3) \qquad (1)$$

where X is a basic functional group; $R_1$, $R_2$, and $R_3$ are each independently an alkyl group; and L is an alkylene group.

4 Claims, 13 Drawing Sheets

(51) Int. Cl.
  *B82Y 30/00* (2011.01)
  *B82Y 40/00* (2011.01)
  *C09K 11/02* (2006.01)
  *G01N 21/17* (2006.01)
  *G01N 21/25* (2006.01)
  *G01N 21/64* (2006.01)

(52) U.S. Cl.
  CPC ............ *G01N 21/648* (2013.01); *B82Y 15/00* (2013.01); *B82Y 30/00* (2013.01); *B82Y 40/00* (2013.01); *G01N 2021/1727* (2013.01); *G01N 2021/258* (2013.01)

(56) References Cited

U.S. PATENT DOCUMENTS

| | | |
|---|---|---|
| 2011/0020241 A1 | 1/2011 | Tsukada et al. |
| 2011/0129942 A1 | 6/2011 | Ohtsuka |
| 2019/0154580 A1 | 5/2019 | Yasuura et al. |

FOREIGN PATENT DOCUMENTS

| | | |
|---|---|---|
| JP | 2009-128136 | 6/2009 |
| JP | 2011-158422 | 8/2011 |
| JP | 2016-020887 | 2/2016 |
| KR | 10-2016-0095387 | 8/2016 |
| WO | 2007/086501 | 8/2007 |
| WO | 2010/016289 | 2/2010 |
| WO | 2015/045961 | 4/2015 |
| WO | 2017/187744 | 11/2017 |

OTHER PUBLICATIONS

I. E. Anderson et al., "Silanization of Low-Temperature-Plasma Synthesized Silicon Quantum Dots for Production of a Tunable, Stable, Colloidal Solution", The Journal of Physical Chemistry C, Jan. 13, 2012, vol. 116, pp. 3979-3987 and Supplementary material.
Minoru Fujii et al., "Silicon quantum dots with heavily boron and phosphorus codoped shell", Chemical Communications, Mar. 30, 2018, vol. 54, pp. 4375-4389.

COMPLEX AND DETECTION DEVICE

BACKGROUND

1. Technical Field

The present disclosure relates to a complex that is to bind specifically to a target substance and a detection device using the complex.

2. Description of the Related Art

A fluorescence method, such as surface plasmon-field enhanced fluorescence spectroscopy, is known as a detection method for highly sensitive detection of a trace amount of target substance. In such a fluorescence method, an organic fluorescent dye is used for labeling a target substance. However, organic fluorescent dyes, which have chemical structurally weak π-bonds, are susceptible to photobleaching. Accordingly, there is a need for fluorescent substances that have stable luminescence characteristics without photobleaching.

Exemplary possible fluorescent substances that have stable luminescence characteristics include luminescent materials formed of inorganic substances. Japanese Unexamined Patent Application Publication No. 2004-83712, for example, discloses a silicon (Si) nanocrystal luminescent material that emits light at ambient temperature and at an energy of Si band gap or less.

Moreover, Japanese Unexamined Patent Application Publication No. 2009-128136, for example, discloses a fluorescence detection method utilizing fluorescent inorganic fine particles as a fluorescent substance. Also see, for example, Japanese Unexamined Patent Application Publication No. 2011-158422.

SUMMARY

The Si nanocrystal luminescent material described in Japanese Unexamined Patent Application Publication No. 2004-83712, however, aggregate when the surface is covered with a silane coupling agent. For this reason, it is difficult to use the Si nanocrystal luminescent material in place of organic fluorescent dyes.

Moreover, the fluorescence detection method described in Japanese Unexamined Patent Application Publication No. 2009-128136 uses fluorescent inorganic fine particles containing a toxic substance, such as Cd (cadmium), Se (selenium), or Te (tellurium). Accordingly, it is difficult to use such fluorescent inorganic fine particles as a fluorescent substance in view of the adverse effects on the human body and the environment.

One non-limiting and exemplary embodiment provides a complex having satisfactory dispersibility and stable luminescence characteristics and containing a fluorescent substance that can reduce adverse effects on the human body and the environment. Further, another non-limiting and exemplary embodiment provides a detection device that can accurately detect a low concentration of target substance by using the complex.

In one general aspect, the techniques disclosed here feature a complex containing: a first substance having a property of specifically binding to a target substance; a quantum dot that contains silicon as a main component and that is negatively charged on a surface; and a linker substance that contains a compound represented by general formula (1) below and that covers the surface of the quantum dot, where the first substance has been immobilized on the surface of the quantum dot through the linker substance:

$$X-L-Si-(R_1)(R_2)(OR_3) \qquad (1)$$

where X is a basic functional group; $R_1$, $R_2$, and $R_3$ are each independently an alkyl group; and L is an alkylene group.

According to the complex of an aspect of the present disclosure, it is possible to realize satisfactory dispersibility and stable luminescence characteristics. Moreover, according to the detection device of another aspect of the present disclosure, it is possible to detect a low concentration of target substance at high sensitively by using the complex.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Findings Underlying the Present Disclosure

Figure 1:
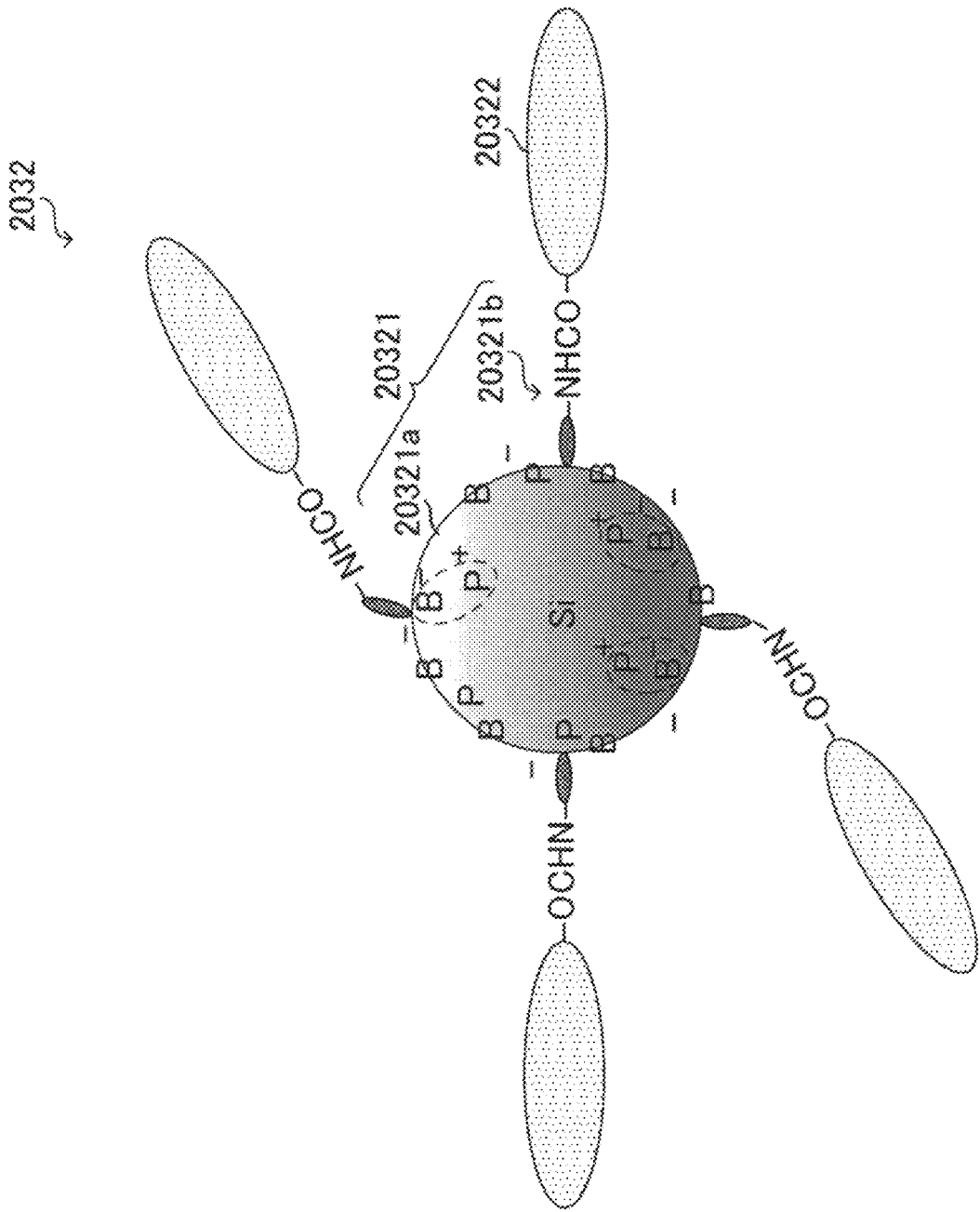
FIG. 1 schematically illustrates an exemplary complex according to Embodiment 1.

As in the foregoing, a fluorescence method has conventionally employed an organic fluorescent dye as a fluorescent substance. In the biological field, for example, detection of biological substances, such as proteins and DNA, or imaging of cells is performed using a labeled antibody, in which an antibody that is to bind specifically to a target substance has been labeled with a fluorescent substance.

However, organic fluorescent dyes have a problem of poor light stability due to the chemical structurally weak π-bonds. For this reason, when an organic fluorescent dye is used, the intensity of irradiation light, the irradiation time, and the like are restricted. Moreover, since the total fluorescence emitted from an organic fluorescent dye decreases over time, it is difficult to detect cumulative fluorescence over time. Further, since an organic fluorescent dye has a small difference between the excitation wavelength and the emission wavelength (so-called Stokes shift), it is difficult to completely block the excitation light with an optical filter during detection of fluorescence. For these reasons, it is difficult to enhance the sensitivity of sensors.

Meanwhile, quantum dots are known as luminescent substances without photobleaching. Quantum dots are formed of inorganic materials and thus exhibit higher light stability than organic fluorescent dyes. In addition, quantum dots have a larger Stokes shift than organic fluorescent dyes. For these reasons, the sensitivity of sensors is expected to be enhanced by using quantum dots as a fluorescent substance in place of an organic fluorescent dye. However, most of conventional quantum dots contain cadmium and thus pose concerns about adverse effects on the human body and the environment. For this reason, quantum dots have been solely used for research purposes and have not yet widely been put into practical use.

Against a backdrop of such circumstances, silicon quantum dots have been attracting attention in recent years. Silicon is an element abundant in Earth's crust as well as exhibits high compatibility with the human body and the environment. For these reasons, silicon quantum dots are attracting attention as promising materials and expected to be put into practical use in the real world.

For example, Japanese Unexamined Patent Application Publication No. 2004-83712 discloses a Si nanocrystal luminescent material (hereinafter, referred to as silicon quantum dots) whose surface is negatively charged by doping boron (B) and phosphorus (P) into the surface. Due to the negatively charged surface, electrostatic repulson results between a plurality of the silicon quantum dots. For this reason, even without surface covering with an organic molecule, in other words, even without surface modification with an organic molecule, the silicon quantum dots exhibit satisfactory dispersibility in aqueous solvents. Further, the silicon quantum dots emit light in the near-infrared region in a stable manner regardless of the surface state. Accordingly, if it is possible to apply such properties to biosensors, the sensitivity of the biosensors is expected to be increased.

For the application to biosensors, silicon quantum dots are required to have the following three features.

The first feature is satisfactory dispersing in aqueous solvents. In nonaqueous solvents, biomaterials undergo irreversible structural changes, such as denaturation of proteins. For this reason, when handling biomaterials, aqueous solvents, such as phosphate-buffered saline (PBS), are used. Accordingly, silicon quantum dots preferably exhibit satisfactory dispersibility in aqueous solvents.

The second feature is satisfactory dispersing in aqueous solvents even without surface covering with an organic molecule or the like in view of the degree of freedom in bonding with a biomaterial. When the surface of silicon quantum dots is covered with an organic molecule or the like, the degree of freedom in bonding with a biomaterial is limited. Accordingly, silicon quantum dots preferably exhibit satisfactory dispersibility in aqueous solvents even without surface covering with an organic molecule or the like.

The third feature is stable light emission in the near-infrared region regardless of the surface state in view of transmission properties in biomaterials.

Meanwhile, many of conventional silicon quantum dots are surface-modified with an organic molecule to ensure satisfactory dispersibility. Consequently, the degree of freedom in bonding between silicon quantum dots and a biomaterial is limited. In other words, since silicon quantum dots are surface-covered with an organic molecule, surface modification of the silicon quantum dots with a linker substance, which is for linking a biomaterial (antibody, for example) with the surface of the silicon quantum dots, is restricted. For this reason, conventional silicon quantum dots are difficult to achieve both satisfactory dispersibility and satisfactory bonding properties with a biomaterial. Moreover, due to light emission caused by oxygen deficiency on the surface, conventional silicon quantum dots tend to greatly vary in luminescence characteristics depending on the surface state, in other words, the state of substances adsorbed onto the surface. Consequently, conventional silicon quantum dots have unstable luminescence characteristics. Further, the emission wavelength is short. Still further, in addition to the above-mentioned problems of silicon quantum dots, porous silicon quantum dots, due to the large particle size, could be detrimental when applied to a biosensor. Such porous silicon quantum dots have a larger particle size than the above-described silicon quantum dots. Accordingly, when a porous silicon quantum dot is used as a labeling substance for labeling an antibody, the porous silicon quantum dot bonded with the antibody (labeled antibody) inhibits the binding of the labeled antibody to an antigen in some cases.

In view of the above, when silicon quantum dots are applied to biosensors, the foregoing problems need to be resolved. To achieve satisfactory bonding properties between a silicon quantum dot and a biomaterial (antibody, for example), Japanese Unexamined Patent Application Publication No. 2009-128136, for example, proposes that a fluorescent quantum dot containing an inorganic material selected from the group consisting of 80 nm or less of ZnSe (zinc selenide), ZnTe (zinc telluride), CdS (cadmium sulfide), CdSe (cadmium selenide), CdTe (cadmium telluride), GaAs (gallium arsenide), Si (silicon), Ag (silver), Au (gold), Fe (iron), Pt (platinum), and Co (cobalt) is bonded with an antibody through a silane coupling agent having a functional group at the terminal.

In the fluorescence detection method described in Japanese Unexamined Patent Application Publication No. 2009-128136, however, fluorescent quantum dots containing a toxic substance, such as Cd, Se, or Te, are used. Accordingly, in view of the adverse effects on the human body and the environment, it is difficult to use such quantum dots as a fluorescent substance.

Meanwhile, the silicon quantum dots described in Japanese Unexamined Patent Application Publication No. 2004-83712 are formed from silicon as a main component and thus can reduce adverse effects on the human body and the environment. Moreover, the silicon quantum dots without surface modification with an organic molecule exhibit satisfactory dispersibility in aqueous solvents due to the negatively charged surface. However, when surface-modified with a linker substance (silane coupling agent, for example), the silicon quantum dots immediately aggregate to form agglomerates. When silicon quantum dots aggregate like this, the detection sensitivity of biosensors decreases since fewer silicon quantum dots are available as fluorescent substances. Accordingly, to enhance the sensitivity of biosensors by exploiting the characteristics as a luminescent substance without photobleaching, silicon quantum dots need to be unsusceptible to aggregation even when surface-modified with a linker substance, in other words, to maintain satisfactory dispersibility.

However, it is difficult to obtain, by the above-described conventional technique, silicon quantum dots surface-modified with a silane coupling agent while maintaining dispersibility and luminescence characteristics. In view of the foregoing problems, the inventor of the present disclosure found, as a result of intensive studies, a complex that contains a silicon quantum dot having satisfactory dispersibility and stable luminescence characteristics as a fluorescent substance. The findings by the present inventor are as follows.

The silicon quantum dots described in Japanese Unexamined Patent Application Publication No. 2004-83712 vary in surface charge state (hereinafter, referred to as charged state) in some cases when surface-modified with a silane coupling agent. In other words, depending on the molecular structure and the amount of a silane coupling agent, the negative charge on the surface of the silicon quantum dots decreases, thereby weakening electrostatic repulsion between the silicon quantum dots. Consequently, silicon quantum dots surface-modified with a silane coupling agent aggregate. For example, when a silane coupling agent has a basic functional group, silicon quantum dots surface-modified with the silane coupling agent aggregate in aqueous solvents due to weakened electrostatic repulsion between the silicon quantum dots when the surface negative charge of the silicon quantum dots decreases to a predetermined value or lower. Meanwhile, a silanol group of a silane coupling agent bonds with a silicon quantum dot. Accordingly, a silane coupling agent having a plurality of silanol groups within the molecule is expected to provide the advantage that more silane coupling agents modify the surface of silicon quantum dots, in other words, more silane coupling agents are fixed to the surface of silicon quantum dots compared with a silane coupling agent having only one silanol group. Meanwhile, there is also the disadvantage that could be caused by having a plurality of silanol groups. For example, it is possible that a plurality of silanol groups of a silane coupling agent could bond with different silicon quantum dots. In this case, a plurality of silicon quantum dots bond with each other through the silane coupling agent and thus result in aggregation. Moreover, it is also possible, for example, that silanol groups without bonding with silicon quantum dots, among a plurality of silanol groups of a silane coupling agent, could bond with silanol groups of other silane coupling agents to form crosslinks between the silane coupling agents. In this case, when silane coupling agents that surface-modify different silicon quantum dots form crosslinks, these silicon quantum dots aggregate.

In view of the above, the present inventor found possible to maintain satisfactory dispersibility and stable luminescence characteristics of silicon quantum dots even when surface-modified with a silane coupling agent by controlling: the type of functional group (i.e., the charging type of the functional group in aqueous solvents) of the silane coupling agent, which is used for surface modification of the silicon quantum dots; the number of silanol groups; and a mixing ratio in the number of molecules between the silicon quantum dots and the silane coupling agent. Further, the present inventor also found possible to detect a low concentration of substance to be detected (hereinafter, referred to as target substance) at higher sensitivity and higher accuracy than conventional biosensors by using, in place of conventional organic fluorescent substances, silicon quantum dots surface-modified with a silane coupling agent in a fluorescence method. This makes it possible to realize a biosensor that enables highly reliable detection.

SUMMARY OF THE PRESENT DISCLOSURE

An aspect of the present disclosure is summarized as follows.

The complex according to an aspect of the present disclosure is a complex containing: a first substance having a property of specifically binding to a target substance; a quantum dot that contains silicon as a main component and that is negatively charged on a surface; and a linker substance that contains a compound represented by general formula (1) below and that covers the surface of the quantum dot, where the first substance has been immobilized on the surface of the quantum dot through the linker substance:

$$X—L—Si—(R_1)(R_2)(OR_3) \qquad (1)$$

where X is a basic functional group; $R_1$, $R_2$, and $R_3$ are each independently an alkyl group; and L is an alkylene group.

Since the linker substance contains a compound having a basic functional group and has one silanol group within the molecule, quantum dots do not bond with each other through the linker substance even when the surface of the quantum dots are covered with the linker substance containing the compound represented by general formula (1) above. In other words, the linker substance represented by general formula (1) above having only one silanol group within the molecule cannot bond with other quantum dots after bonding with one quantum dot. For this reason, even when the surface of quantum dots is covered with the linker substance containing the compound represented by general formula (1) above, the quantum dots are less likely to aggregate. Consequently, the complex according to an aspect of the present disclosure exhibits satisfactory dispersibility. Herein, a basic functional group is, for example, a proton-withdrawing functional group and an electron-donating functional group. In other words, a basic functional group is a positively charged functional group when ionized. Further, the quantum dots formed from an inorganic material exhibit higher light resistance than organic fluorescent substances. For this reason, the quantum dots are less susceptible to photobleaching. Accordingly, the complex of an aspect of the present disclosure has stable luminescence characteristics. In addition, silicon as a main component of the quantum dots has extremely low adverse effects on the human body and the environment. Accordingly, the complex of an aspect of the present disclosure can reduce adverse effects on the human body and the environment. Further, silicon accounts for about 28% of the Earth's crust and is the second most abundant element after oxygen. For this reason, by incorporating silicon as a main component into quantum dots, the complex according to an aspect of the present disclosure not only contributes to environmental conservation (sustainability) into the future but also can realize lower costs.

In the complex according to an aspect of the present disclosure, for example, X in general formula (1) above may be an amino group.

By having such a structure, the linker substance exhibits high bonding properties with the first substance, for example, when the first substance has a carboxy group at the terminal. For this reason, it is possible to satisfactorily bond a quantum dot with the first substance through the linker substance. Consequently, the stability of the complex according to an aspect of the present disclosure is enhanced.

In the complex according to an aspect of the present disclosure, for example, $R_1$ and $R_2$ may be a methyl group, $R_3$ may be an ethyl group, and L may be a propylene group.

Since the linker substance has only one silanol group within the molecule as in the foregoing, quantum dots are less likely to aggregate even if the linker substance has a basic functional group, in other words, has a functional group to be cationized. For this reason, the complex according to an aspect of the present disclosure maintains satisfactory dispersibility.

In the complex according to an aspect of the present disclosure, for example, the surface of the quantum dot may contain boron and phosphorus.

By having such constitution, the quantum dot is negatively charged. Consequently, quantum dots are less likely to aggregate due to electrostatic repulsion between the quantum dots. For this reason, the complex according to an aspect of the present disclosure exhibits satisfactory dispersibility.

Further, the detection device according to an aspect of the present disclosure detects, using any of the above-described complexes, the target substance by labeling the target substance.

As in the foregoing, quantum dots are less susceptible to photobleaching. For this reason, a complex containing such a quantum dot as a constituent maintains stable luminescence characteristics even when irradiated with high-intensity light. Accordingly, by labeling the target substance with the complex, the detection device according to an aspect of the present disclosure can detect a low concentration of the target substance at high sensitivity. Moreover, the complex maintains stable luminescence characteristics even under continuous irradiation with light. For this reason, the detection device according to an aspect of the present disclosure can detect the target substance by calculating or summing changes in the target substance over time. Accordingly, by using any of the above-described complexes, the detection device according to an aspect of the present disclosure enables highly reliable detection. Further, quantum dots have a larger Stokes shift than conventional organic fluorescent dyes. For this reason, when quantum dots are used as a fluorescent substance, it is possible to pass fluorescence alone through an optical filter while blocking excitation light. Accordingly, by using any of the above-described complexes, the detection device according to an aspect of the present disclosure can detect a low concentration of target substance at high accuracy.

The detection device according to an aspect of the present disclosure may include, for example, a holder for holding a base material on which a second substance having a property of specifically binding to the target substance has been immobilized; a feeder for introducing the complex and a sample that potentially contains the target substance into the holder; an irradiator for irradiating the holder with excitation light; and a detector for detecting the target substance on the basis of light emitted from the complex due to the excitation light with which the holder is irradiated.

By the above configuration, a sandwich structure in which the second substance immobilized on the base material, the target substance, and the first substance in the complex are bonded in this order is formed in the holder. Accordingly, the detection device according to an aspect of the present disclosure can detect a low concentration of the target substance at high sensitivity by detecting light emitted from the complex in the sandwich structure.

In the detection device according to an aspect of the present disclosure, for example, the base material may enhance the light emitted from the complex by plasmon resonance that occurs on the surface of the base material.

Consequently, the detection device according to an aspect of the present disclosure can detect a low concentration of target substance at high sensitivity.

In the detection device according to an aspect of the present disclosure, for example, the base material may be a substrate having a metal fine structure on the surface of the base material.

Consequently, since localized plasmon occurs on the surface of the substrate, light emitted from the complex is enhanced by plasmon resonance. For this reason, the detection device according to an aspect of the present disclosure can detect a low concentration of target substance at high sensitivity.

For example, the detection device according to an aspect of the present disclosure may further include an applicator for generating a magnetic field in the holder, where the base material may be a magnetic fine particle and may be configured to move in a predetermined direction in response to the magnetic field generated by the applicator.

By the above constitution, the sandwich structure, in which the first substance in the complex, the target substance, and the second substance immobilized on the surface of the base material are bonded in this order, moves in a predetermined direction within the holder in response to a magnetic field generated by the applicator. On this occasion, when the holder is irradiated with excitation light, the complex in the sandwich structure emits fluorescence. Consequently, the detection device according to an aspect of the present disclosure can detect the sandwich structure that moves in a predetermined direction as the movement of a light spot. Moreover, since formed from an inorganic material, the quantum dot in the complex is less susceptible to photobleaching. For this reason, the quantum dot maintains stable luminescence characteristics while the sandwich structure moves in a predetermined direction in response to a magnetic field even under continuous irradiation with excitation light. Accordingly, the detection device of an aspect of the present disclosure can detect a low concentration of target substance at high accuracy.

It should be noted that general or specific embodiments may be implemented as a system, a method, an integrated circuit, a computer program, a computer-readable recording medium, such as CD-ROM, or any selective combination thereof.

Hereinafter, embodiments will be concretely described in reference to the drawings.

All the embodiments described hereinafter are general or specific examples. Accordingly, numerical values, shapes, materials, components, arrangement positions and connection modes of the components, steps, the order of the steps, and so forth in the following embodiments are exemplary and are not intended to limit the scope of the claims. Moreover, among components in the following embodiments, components that are not recited in independent claims, which represent the broadest concepts, will be described as optional components.

Further, each figure is not necessarily illustrated precisely. In each figure, substantially same components are denoted by the same sign, and repetitive explanations will be omitted or simplified.

Embodiment 1

Hereinafter, a complex and a detection device using the complex according to Embodiment 1 will be described.

Complexes

Figure 2:
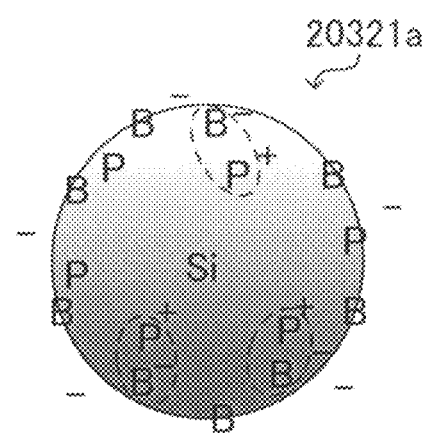
FIG. 2 schematically illustrates an exemplary quantum dot of Embodiment 1.
Figure 3:
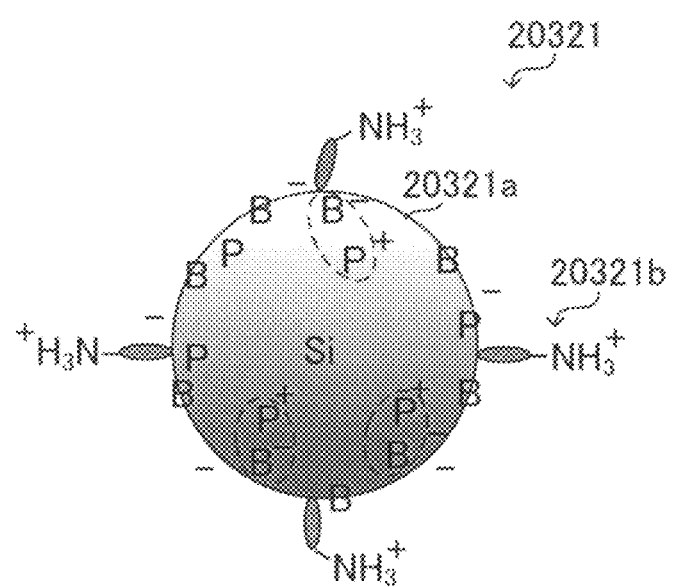
FIG. 3 schematically illustrates an exemplary surface-modified quantum dot of Embodiment 1.

First, the complex according to Embodiment 1 will be concretely described in reference to FIGS. 1 to 3. FIG. 1 schematically illustrates an exemplary structure of a complex 2032 according to Embodiment 1.

As illustrated in FIG. 1, the complex 2032 includes a first substance 20322, a quantum dot 20321a, and a linker substance 20321b. The first substance 20322 has the property of specifically binding to a target substance to be detected. Exemplary target substances include proteins, lipids, sugars, and nucleic acids. Exemplary substances having the property of specifically binding to target substances include antibodies for antigens, enzymes for substrates or coenzymes, receptors for hormones, protein A or protein G for antibodies, avidins for biotin, calmodulin for calcium, and lectins for carbohydrates. For example, when a target substance is a protein, such as a virus component, the first substance 20322 is, for example, an antibody against the protein as an antigen. The first substance 20322 has been immobilized on the surface of the quantum dot 20321a through the linker substance 20321b. Since the linker substance 20321b will be described hereinafter, the explanation thereof is omitted here.

Quantum Dots

FIG. 2 schematically illustrates an exemplary structure of the quantum dot 20321a of Embodiment 1. The quantum dot 20321a contains silicon (Si) as a main component and is negatively charged on the surface. The surface of the quantum dot 20321a contains boron (B) and phosphorus (P). Here, boron is an n-type impurity and phosphorus is a p-type impurity.

The production process for the quantum dot 20321a includes, for example, forming a film of a composite (hereinafter, referred to as BPSG: borophosphosilicate glass) comprising Si, $SiO_2$, $B_2O_3$, and $P_2O_5$ on a substrate surface by sputtering; and subsequently heat-treating the BPSG film in an inert gas atmosphere in a temperature range of 1,100° C. to 1,300° C. for a predetermined time. Consequently, silicon nanocrystals are formed within the BPSG film. Here, through heat treatment of the BPSG film, an n-type impurity (here, boron) and a p-type impurity (here, phosphorus) are simultaneously doped into the silicon nanocrystals. The particle size of the quantum dot 20321a, as a major axis, is 0.5 nm or more and 10 nm or less and may be 3 nm or more and 5 nm or less.

The amounts of boron and phosphorus doped into silicon nanocrystals may be appropriately adjusted depending on the purposes. The surface negative charge of quantum dots is adjusted by the amounts of boron and phosphorus doped.

FIG. 3 schematically illustrates an exemplary structure of a surface-modified quantum dot 20321 of Embodiment 1 in which the quantum dot 20321a is surface-modified with the linker substance 20321b. The linker substance 20321b contains a compound represented by general formula (1) below and covers the surface of the quantum dot 20321a:

$$X\text{---}L\text{---}Si\text{---}(R_1)(R_2)(OR_3) \quad (1)$$

where X is a basic functional group; $R_1$, $R_2$, and $R_3$ are each independently an alkyl group; and L is an alkylene group.

Here, the basic functional group is a Bronsted basic functional group. Such a Bronsted basic functional group acts as a proton acceptor. In other words, the basic functional group is a proton-withdrawing functional group, an electron-donating functional group, and a positively charged functional group when ionized. Exemplary basic functional groups include primary amino groups, secondary amino groups, tertiary amino groups, and quaternary ammonium groups. The basic functional group may be a primary amino group (hereinafter, referred to as amino group) or a secondary amino group. Particularly, X in general formula (1) above may be an amino group. When X in general formula (1) is an amino group, the linker substance 20321b forms a peptide bond (—CONH—) with a carboxy group of the first substance 20322.

Further, $R_1$, $R_2$, and $R_3$ in general formula (1) above are each independently an alkyl group. Consequently, the linker substance 20321b has one silanol group within the molecule. $R_1$, $R_2$, and $R_3$ are a substituted or unsubstituted alkyl group and include a linear or branched alkyl group having 5 or less carbon atoms. Particularly, the alkyl group may have 1 or more and 3 or less carbon atoms. Exemplary unsubstituted alkyl groups having 3 or less carbon atoms include a methyl group, an ethyl group, a propyl group, and an isopropyl group. Particularly, $R_1$ and $R_2$ may be a methyl group having 1 carbon atom, and $R_3$ may be an ethyl group having 2 carbon atoms.

The alkyl group may further have a substituent. Exemplary substituents include an alkyl group, an alkoxy group, a hydroxy group, and an ester group. Exemplary hydroxy-substituted alkyl groups include a methylol group and a hydroxybutyl group. Exemplary ester-substituted alkyl groups include a methoxycarbonyl group, an ethoxycarbonyl group, a propoxycarbonyl group, and an isopropoxycarbonyl group.

L in general formula (1) above is a substituted or unsubstituted alkylene group, and the number of carbon atoms may be 10 or less. Particularly, the number of carbon atoms may be 1 or more and 5 or less. The —$CH_2$— of the alkylene group of L may be replaced with one or more groups selected from the group consisting of an imino group (—NH—), an ester group (—COO—), an ether group (—O—), and a phenylene group. Particularly, L may be a propylene group having 3 carbon atoms. Exemplary unsubstituted alkylene groups include a methylene group, an ethylene group, a propylene group, and a butylene group. The substituted alkylene group is an alkylene group having at least one substituent, for example. Exemplary substituents include an alkyl group, an alkoxy group, a hydroxy group, and an ester group.

Production Process for Complexes

Figure 4:
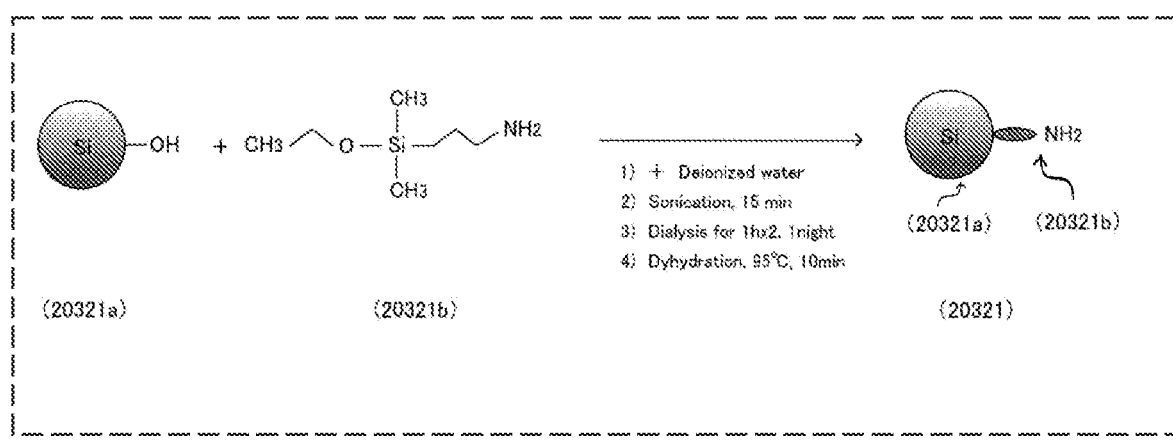
FIG. 4 shows an exemplary production process for the surface-modified quantum dot of Embodiment 1.
Figure 5:
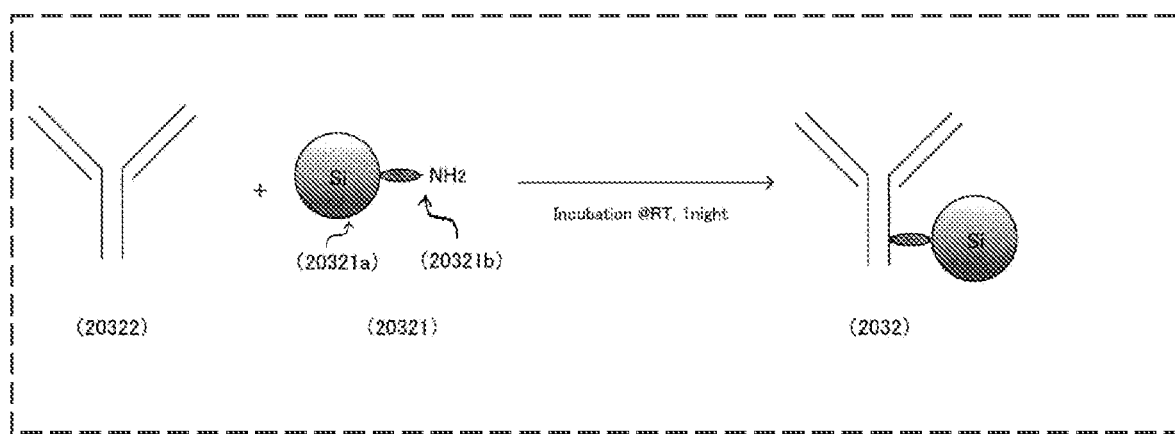
FIG. 5 shows an exemplary production process for the complex according to Embodiment 1.

Next, the production process for the complex 2032 will be concretely described in reference to FIGS. 4 and 5. FIG. 4 shows an exemplary production process for the surface-modified quantum dot 20321 of Embodiment 1.

The surface-modified quantum dot 20321 includes the linker substance 20321b that contains a compound represented by structural formula (2) below and that covers the surface of the quantum dot 20321a. The compound represented by the structural formula (2) below is APDMES (3-aminopropyldimethylethoxysilane).

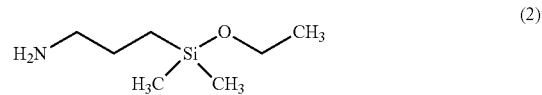

As shown in FIG. 4, the quantum dot 20321a and the linker substance 20321b are mixed first, [1] added with deionized water, [2] subjected to sonication for 15 minutes, then subjected to [3] dialysis for 1 hour twice, left standing overnight, and [4] subjected to dehydration at 95° C. for 10 minutes. Through this process, the surface-modified quantum dot 20321 in which the quantum dot 20321a has been surface-modified with the linker substance 20321b is obtained.

FIG. 5 shows an exemplary production process for the complex 2032 according to Embodiment 1. As shown in FIG. 5, the complex 2032 is prepared by incubating, at room temperature overnight, the first substance 20322 (IgG antibody, for example), which is to bind specifically to a target substance, and the surface-modified quantum dot 20321 obtained by the production process shown in FIG. 4. In this process, to bond the first substance 20322 and the surface-modified quantum dot 20321 further efficiently, activation treatment may be performed using a substance (hereinafter, referred to as reaction-promoting substance) that promotes bonding reactions between the first substance 20322 and the surface-modified quantum dot 20321. Exemplary reaction-promoting substances include DMT-MM (4-(4,6-dimethoxy-1,3,5-triazin-2-yl)-4-methyl-morpholinium chloride n-hydrate) and EDC (1-ethyl-3-(3-dimethylaminopropyl) carbodiimide hydrochloride)-sulfo-NHS (N-hydroxysulfosuccinimide). In the example shown in FIG. 5, the surface-modified quantum dot 20321 and the first substance 20322 are bonded through a peptide bond in the complex 2032. Here, FIGS. 4 and 5 show the production process for the complex 2032 using an exemplary linker substance 20321b in which X in general formula (1) is an amino group. However, X may be any basic substituent and is not limited to an amino group. Moreover, the production process is an example in which the linker substance 20321b has one silanol group within the molecule but is not limited thereto. Further, as the method of bonding the surface-modified quantum dot 20321 and the first substance 20322, other publicly known methods may be employed unless the first substance 20322 is deactivated.

Dispersibility Evaluation of Surface-Modified Quantum Dots

Next, the dispersibility of surface-modified quantum dots were evaluated.

EXAMPLES 1 to 3

In the following Examples, the compound (APDMES) represented by structural formula (2) above was used as a linker substance. As shown in structural formula (2), APDMES has an amino group (—NH$_2$ group) as a basic functional group and one silanol group. As quantum dots, phosphorus- and boron-doped silicon fine particles having a particle size of 3.9 nm were used. Further, as a substance that promotes reactions between the quantum dots and the linker substance, DMT-MM was used.

Figure 6:
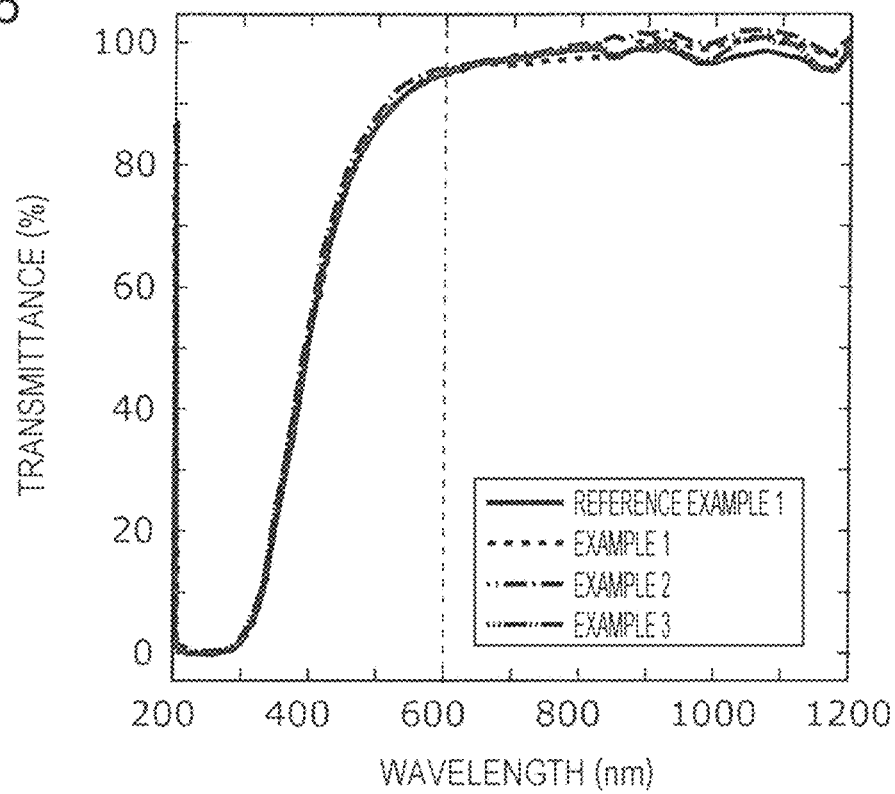
FIG. 6 is a graph showing the measured results of light transmittance for aqueous dispersions of surface-modified quantum dots according to Examples 1 to 3.

Surface-modified quantum dots according to Examples 1 to 3 were prepared in accordance with the production process shown in FIG. 4 by mixing the respective quantum dots with the linker substance at a mixing ratio of 1:125, 1:250, and 1:1250 (the number of quantum dots: the number of linker substance molecules), respectively. Subsequently, the respective surface-modified quantum dots according to Examples 1 to 3 were dispersed in water to prepare dispersions (hereinafter, referred to as aqueous dispersions of the surface-modified quantum dots according to Examples 1 to 3). Light transmittance was measured for these dispersions using a spectrophotometer (UV-1600, Shimadzu Corporation). Concretely, 100 µL of each dispersion was fed to a microcell, and light transmittance of the dispersion was measured in the wavelength range of 200 nm to 800 nm. The results are shown in FIG. 6. FIG. 6 is a graph showing the measured results of light transmittance for the aqueous dispersions of the surface-modified quantum dots according to Examples 1 to 3. Here, light transmittance was also measured for an aqueous dispersion of quantum dots without surface modification as Reference Example 1.

As shown in FIG. 6, the respective aqueous dispersions of the surface-modified quantum dots according to Examples 1 to 3 exhibit light transmittance roughly comparable to Reference Example 1 in the entire wavelength range measured.

The quantum dots used in the Examples do not absorb light in the wavelength range of 600 nm or more. Accordingly, if the quantum dots have satisfactory dispersibility in an aqueous dispersion, the aqueous dispersion exhibits high light transmittance in the wavelength range of 600 nm or more. Since the aqueous dispersions of the surface-modified quantum dots according to Examples 1 to 3 exhibit high light transmittance in the wavelength range of 600 nm or more, it was confirmed that macroscopic scattering objects (i.e., agglomerates) were not formed in these dispersions. This revealed that the surface-modified quantum dots according to Examples 1 to 3 have satisfactory dispersibility in an aqueous solvent.

COMPARATIVE EXAMPLES 1 TO 3

In the following Comparative Examples, the compound (APTMS: 3-aminopropyltrimethoxysilane) represented by structural formula (3) below was used as a linker substance.

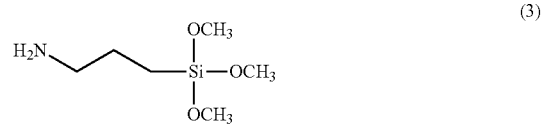 [SMILES: CO[Si](CCCN)(OC)OC]

(3)

As shown in structural formula (3) above, APTMS has an amino group (—NH$_2$ group) as a basic functional group and three silanol groups (i.e., three Si—O bonds).

Figure 7:
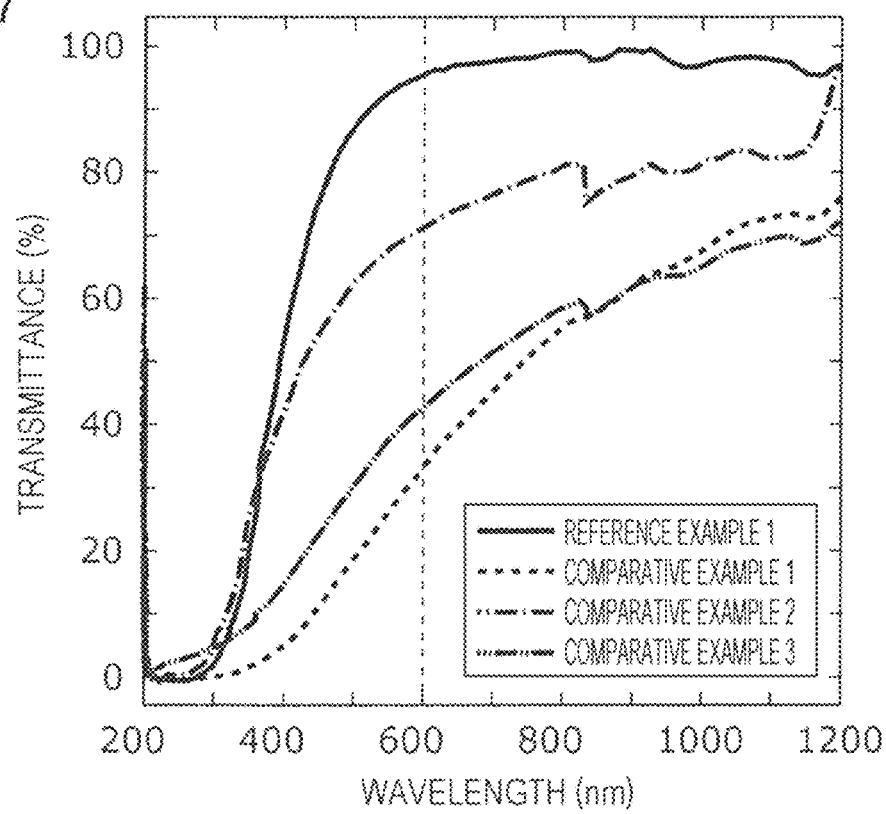
FIG. 7 is a graph showing the measured results of light transmittance for aqueous dispersions of surface-modified quantum dots according to Comparative Examples 1 to 3.

Surface-modified quantum dots according to Comparative Examples 1 to 3 were prepared in the same manner as Examples 1 to 3 except for using APTMS as a linker substance. Subsequently, the respective surface-modified quantum dots according to Comparative Examples 1 to 3 were dispersed in water to prepare dispersions (hereinafter, referred to as aqueous dispersions of the surface-modified quantum dots according to Comparative Examples 1 to 3). Light transmittance was measured for these dispersions in the same manner as Examples 1 to 3. The results are shown in FIG. 7. FIG. 7 is a graph showing the measured results of light transmittance for the aqueous dispersions of the surface-modified quantum dots according to Comparative Examples 1 to 3. Here, light transmittance was also measured for an aqueous dispersion of quantum dots without surface modification as Reference Example 1.

As shown in FIG. 7, the respective aqueous dispersions of the surface-modified quantum dots according to Comparative Examples 1 to 3 exhibit lower light transmittance than Reference Example 1 in the entire wavelength range measured. Since the aqueous dispersions of the surface-modified quantum dots according to Comparative Examples 1 to 3 exhibit considerably lower light transmittance than Reference Example 1 in the wavelength range of 600 nm or more, it was confirmed that macroscopic scattering objects (i.e., agglomerates) were formed in these aqueous dispersions.

This revealed that the surface-modified quantum dots according to Comparative Examples 1 to 3 aggregate in an aqueous solvent.

Dispersibility Evaluation of Complexes

Subsequently, the dispersibility of complexes was evaluated.

EXAMPLE 4

Figure 8:
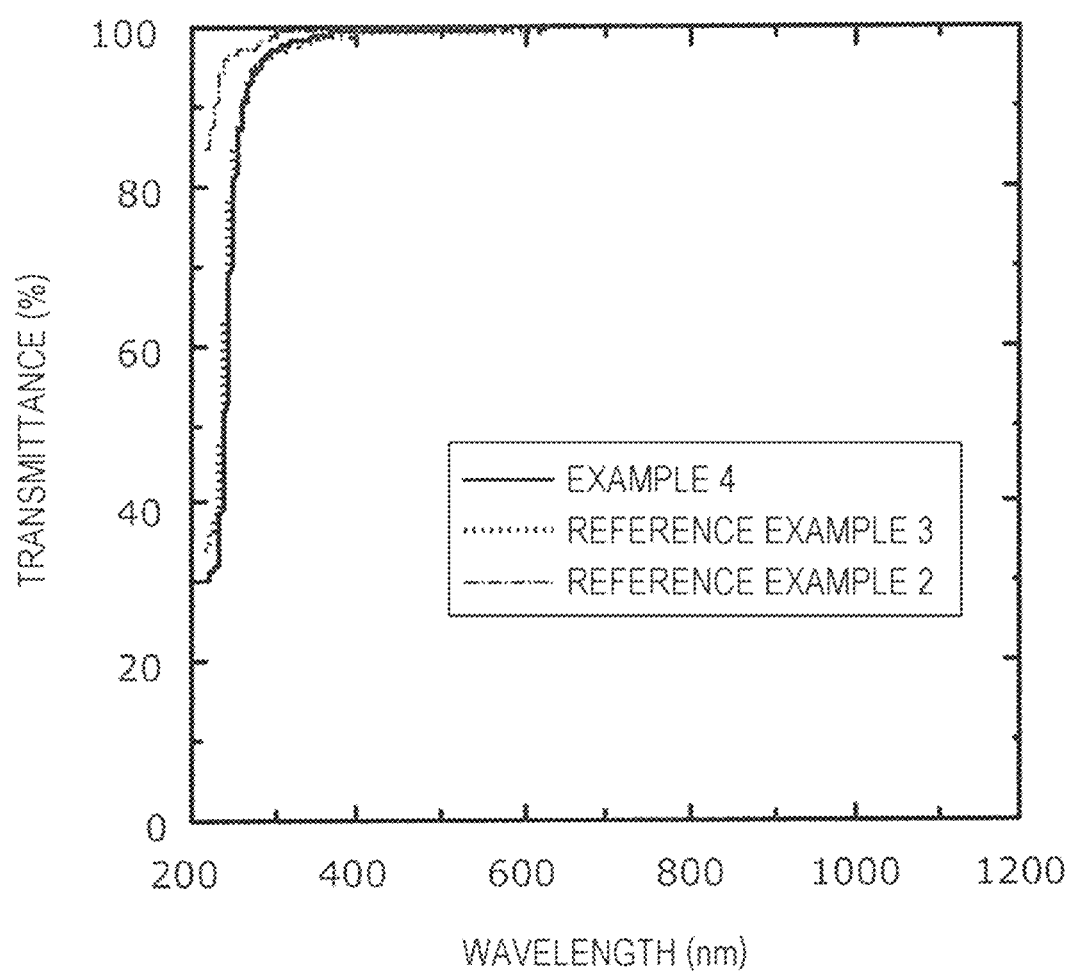
FIG. 8 is a graph showing the measured results of light transmittance for a dispersion of complexes according to Example 4.

In accordance with the production process shown in FIG. 5, complexes each consisting of the surface-modified quantum dot according to Example 2 bonded with IgG antibody were prepared. The resulting complexes were dispersed in phosphate-buffered saline (PBS) to prepare a dispersion. Light transmittance was measured for the dispersion in the same manner as Examples 1 to 3. The results are shown in FIG. 8. FIG. 8 is a graph showing the measured results of the light transmittance for the dispersion of the complexes according to Example 4. Here, Reference Example 2 is a dispersion in which the surface-modified quantum dots according to Example 2 are dispersed in PBS, and Reference Example 3 is a dispersion in which IgG is dispersed in PBS.

As shown in FIG. 8, the dispersion of the complexes according to Example 4 exhibits light transmittance roughly comparable to the light transmittance of the dispersion of the surface-modified quantum dots according to Reference Example 2. Accordingly, the complexes according to Example 4 were found to exhibit, in an aqueous solvent, dispersibility roughly comparable to that of the surface-modified quantum dots according to Example 2. Moreover, since the dispersion of the complexes according to Example 4 does not exhibit lowering in light transmittance in the wavelength range of 600 nm or more, it was confirmed that macroscopic agglomerates were not formed in the dispersion. This revealed that the complexes according to Example 4 have satisfactory dispersibility in an aqueous solvent.

CONCLUSION

The linker substance used in Examples 1 to 3 has one silanol group within the molecule. Meanwhile, the linker substance used in Comparative Examples 1 to 3 has three silanol groups within the molecule. As described in the "Findings Underlying the Present Disclosure" section, as the number of silanol groups contained within the molecule of a linker substance increases, crosslinks between the linker substance molecules as well as bonds between the linker substance and a plurality of quantum dots are further readily formed. Consequently, a plurality of quantum dots tend to be bonded with each other through the linker substance. For this reason, agglomerates are more likely to be formed as the number of silanol groups contained within the molecule of a linker substance increases. The linker substance (APDMES) used in Examples 1 to 3 has an amino group as a basic functional group within the molecule and is thus positively charged in an aqueous solvent. APDMES, which is charged oppositely to the surface charge of the quantum dots, could weaken the surface negative charge of the quantum dots. However, after bonding with the surface of a quantum dot, APDMES having only one silanol group within the molecule is unlikely to bond with other quantum dots or other linker substance molecules.

In other words, bonding of one linker substance molecule with a plurality of quantum dots as well as crosslinking between linker substance molecules is unlikely to occur. Consequently, even when quantum dots are surface-modified with APDMES, the quantum dots are unlikely to bond with each other through APDMES. For this reason, it is presumed that electrostatic repulsion between the quantum dots was not lowered, thereby ensuring satisfactory dispersibility of the surface-modified quantum dots according to Examples 1 to 3.

Meanwhile, the linker substance (APTMS) used in the Comparative Examples has an amino group as a basic functional group within the molecule as in APDMES but has three silanol groups. Accordingly, even after bonding with the surface of a quantum dot, APTMS can bond with other quantum dots or other linker substance molecules. More concretely, when quantum dots are surface-modified with APTMS, the surface negative charge of the quantum dots is weakened by the positive charge of APTMS, thereby lowering electrostatic repulsive force between the quantum dots. When the electrostatic repulsive force is lowered to a certain degree, it is impossible to suppress bonding between silanol groups that do not bond with the surface of a quantum dot and other quantum dots or linker substances bonded with the surface of other quantum dots. For this reason, it is presumed that satisfactory dispersibility of quantum dots was not ensured for the surface-modified quantum dots according to Comparative Examples 1 to 3.

Regarding the dispersibility of complexes, it was confirmed from the results of Example 4 that if surface-modified quantum dots have satisfactory dispersibility, the surface-modified quantum dots maintain the dispersibility even after bonded with the first substance (antibody, for example).

The foregoing revealed that quantum dots surface-modified with a linker substance having a basic functional group and one silanol group within the molecule can maintain satisfactory dispersibility of the quantum dots regardless of a mixing ratio between the quantum dots and the linker substance. Moreover, it was found that complexes each consisting of the surface-modified quantum dot bonded with the first substance (IgG, for example) can also maintain satisfactory dispersibility in the same manner as the surface-modified quantum dots. Accordingly, it was found possible to obtain complexes that exhibit bonding properties with the first substance while maintaining satisfactory dispersibility of the quantum dots by using a linker substance having a basic functional group and one silanol group within the molecule.

Outline of Detection System

Next, a detection system equipped with the detection device according to Embodiment 1 as a component will be described. The detection device is a device for detecting, using the complex 2032 according to Embodiment 1, a target substance by labeling the target substance. Exemplary target substances include proteins, lipids, sugars, and nucleic acids.

Figure 9:
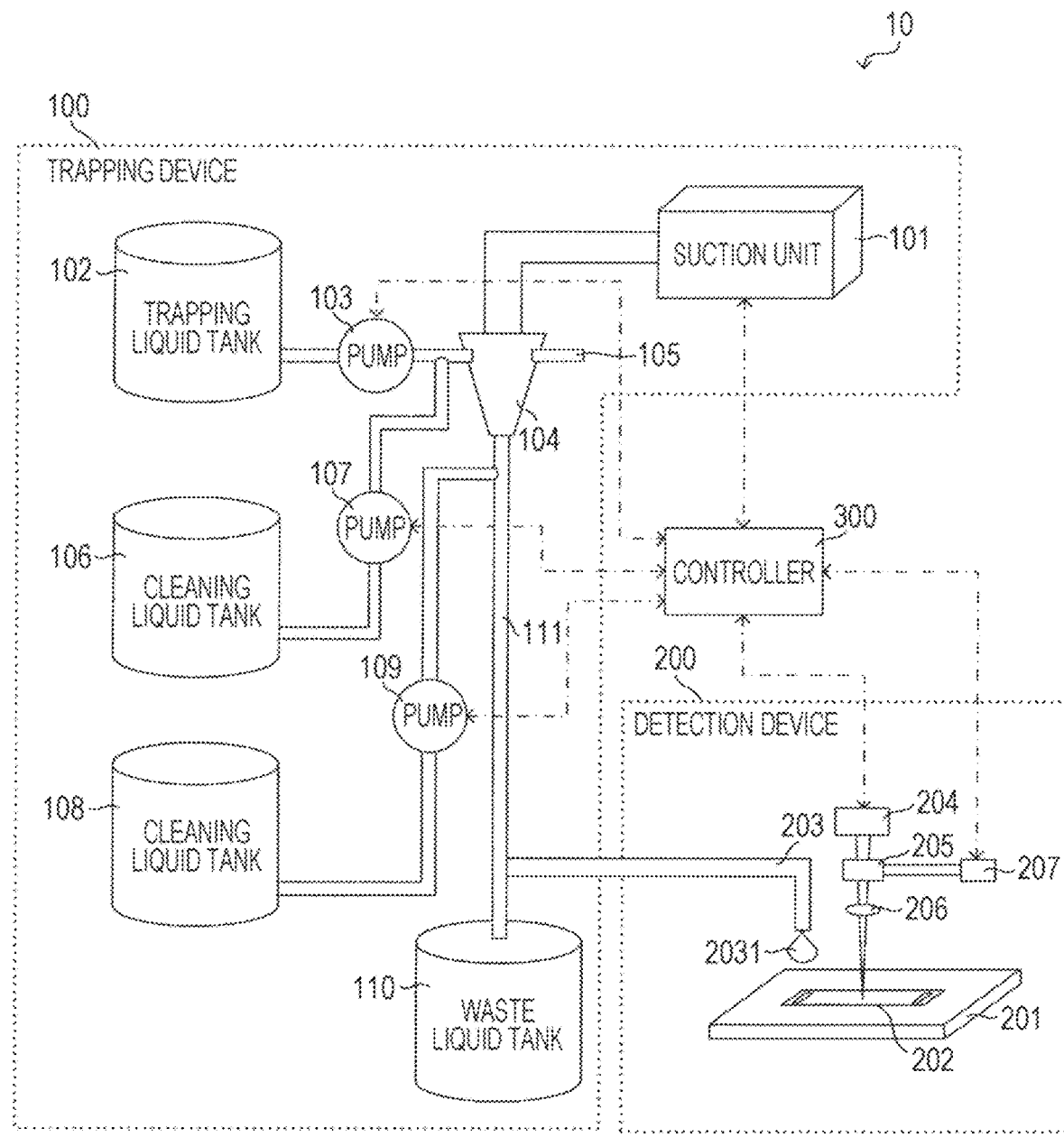
FIG. 9 schematically illustrates an exemplary detection system of Embodiment 1.

FIG. 9 schematically illustrates an exemplary configuration of a detection system 10 of Embodiment 1. The detection system 10 is installed in a room where some people enter and leave frequently, for example. The detection system 10, for example, traps fine particles that potentially include a target substance, such as an airborne virus, and detects the concentration of the target substance included in the fine particles. Hereinafter, the case in which a target substance is a virus or a virus component (hereinafter, simply referred to as virus) will be described. Exemplary virus components include proteins and nucleic acids that constitute a virus. The types of virus are not particularly limited and may be any type that is commonly classified as a virus. Herein, a virus will be described as an exemplary airborne target substance but is not limiting. Such airborne target substances may be bacteria or allergens, such as pollen.

As illustrated in FIG. 9, the detection system 10 includes a trapping device 100, a detection device 200, and a controller 300. Hereinafter, the details of the trapping device 100, the detection device 200, and the controller 300 will be described.

Configuration of Trapping Device

The trapping device 100 traps fine particles that potentially include a virus in air and mixes with a trapping liquid. More concretely, the trapping device 100 traps a virus in air by sucking ambient air through an air inlet port 105, collecting fine particles that potentially include the virus and so forth in air, and mixing with a trapping liquid. As illustrated in FIG. 9, the trapping device 100 includes a suction unit 101, a trapping liquid tank 102, a pump 103, a cyclone 104, an air inlet port 105, a cleaning liquid tank 106, a pump 107, a cleaning liquid tank 108, a pump 109, a waste liquid tank 110, and a liquid channel 111. Hereinafter, each component of the trapping device 100 will be described.

The suction unit 101 sucks ambient air through the air inlet port 105. Consequently, fine particles that potentially include a virus in ambient air is sucked together with air into the cyclone 104 through the air inlet port 105. The suction unit 101 is connected to the cyclone 104 and driven to cause the cyclone 104 to operate.

The trapping liquid tank 102 is a container for holding a trapping liquid for trapping a virus in air.

The pump 103 supplies the trapping liquid in the trapping liquid tank 102 to the cyclone 104.

The cyclone 104 is connected to the air inlet port 105 and the trapping liquid tank 102 and mixes fine particles, which can potentially include a virus in the air sucked by the suction unit 101 through the air inlet port 105, with a trapping liquid supplied by the pump 103 from the trapping liquid tank 102. The cyclone 104 is connected to the detection device 200 through the liquid channel 111. A trapping liquid mixed with fine particles (hereinafter, referred to as sample) is supplied from the cyclone 104 to the detection device 200 through the liquid channel 111.

The cleaning liquid tank 106 is a container for holding a cleaning liquid for cleaning the cyclone 104 and the liquid channel 111. The cleaning liquid tank 106 is connected to the cyclone 104, and a cleaning liquid in the cleaning liquid tank 106 is supplied to the cyclone 104 by the pump 107.

The cleaning liquid tank 108 is a container for holding a cleaning liquid for cleaning the liquid channel 111. The cleaning liquid tank 108 is connected to the liquid channel 111, and a cleaning liquid in the cleaning liquid tank 108 is supplied to the liquid channel 111 by the pump 109.

The waste liquid tank 110 is a container for storing waste liquids. The waste liquid tank 110 stores a cleaning liquid after cleaning the cyclone 104 and the liquid channel 111, for example.

The liquid channel 111 is a channel for guiding a sample discharged from the cyclone 104 to the detection device 200. The liquid channel 111 is connected to a feeder 203 of the detection device 200.

Configuration of Detection Device

Figure 10:
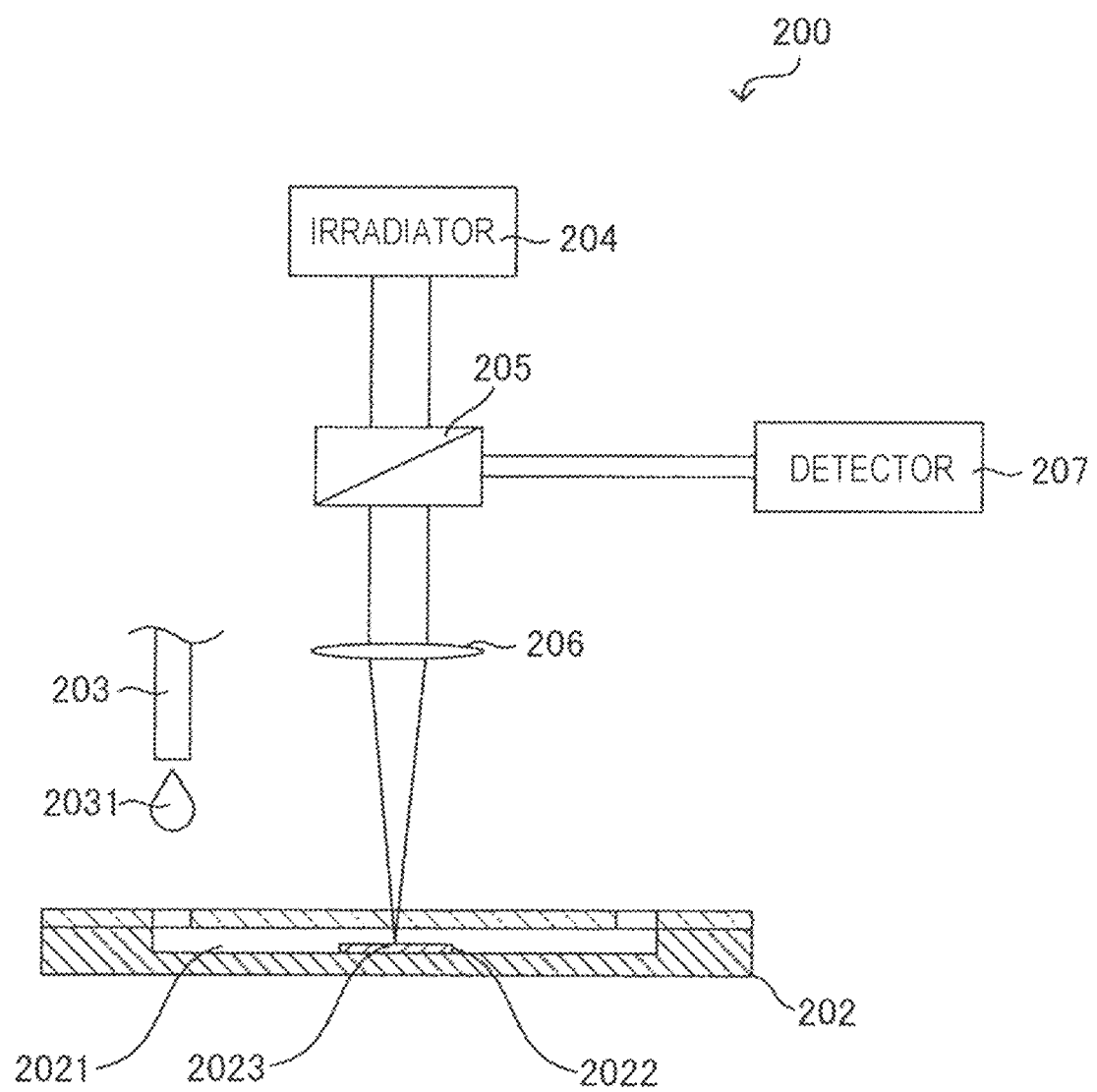
FIG. 10 schematically illustrates an exemplary detection device according to Embodiment 1.

Next, the detection device 200 will be concretely described in reference to FIGS. 9 and 10. FIG. 10 schematically illustrates an exemplary configuration of the detection device 200 according to Embodiment 1.

The detection device 200 according to Embodiment 1 includes: a holder 202 for holding a base material 2022 on which a second substance (antibody, here) having the property of specifically binding to a virus has been immobilized; a feeder 203 for introducing a sample that potentially contains the virus and a complex 2032 (see FIG. 3) into the holder 202; an irradiator 204 for irradiating the holder 202 with excitation light; and a detector 207 for detecting the virus on the basis of light emitted from the complex 2032 due to the excitation light with which the holder is irradiated. The second substance may be the same type of molecule as or a different type of molecule from the first substance in the complex 2032. The first substance and the second substance have the properties of binding to different sites of a target substance. When the first substance and the second substance are the same type of molecules, the first substance and the second substance are, for example, antibodies against a virus as an antigen. In this case, the first substance and the second substance bind to different sites of the virus. Further, when the first substance and the second substance are different types of molecules, the first substance is a coenzyme, for example, and the second substance is a substrate, for example. In this case, a target substance is an enzyme, for example.

The detection device 200 detects a virus in a trapping liquid that has been mixed with fine particles by the trapping device 100. As illustrated in FIGS. 9 and 10, the detection device 200 includes a sensor device 201, a feeder 203, an irradiator 204, a beam splitter 205, a lens 206, and a detector 207. Hereinafter, each component of the detection device 200 will be described.

The sensor device 201 includes a holder 202. Although one holder 202 is included in FIG. 9, the sensor device 201 may include a plurality of holders, In the present embodiment, the sensor device 201 can measure the range for the number of viruses ($10^3$ to $10^6$, for example) in a sample liquid 2031 of a predetermined volume (1 mL, for example). Moreover, the present embodiment utilizes a surface-enhanced fluorescence method to detect the number of viruses optically. Here, when a target substance is a biological substance, such as an enzyme, a hormone, and an immune antibody, the sensor device 201 can measure the concentration of the biological substance in the sample liquid 2031 of a predetermined volume.

As illustrated in FIG. 10, the holder 202 includes a channel 2021 and a base material 2022.

The channel 2021 is a channel for guiding the sample liquid 2031 fed in drops from the feeder 203 to a detection region 2023. The channel 2021 has a feed port for supplying the sample liquid 2031 into the channel 2021 and a discharge port for discharging the sample liquid 2031 in the channel 2021 outside the holder 202.

Figure 11A:
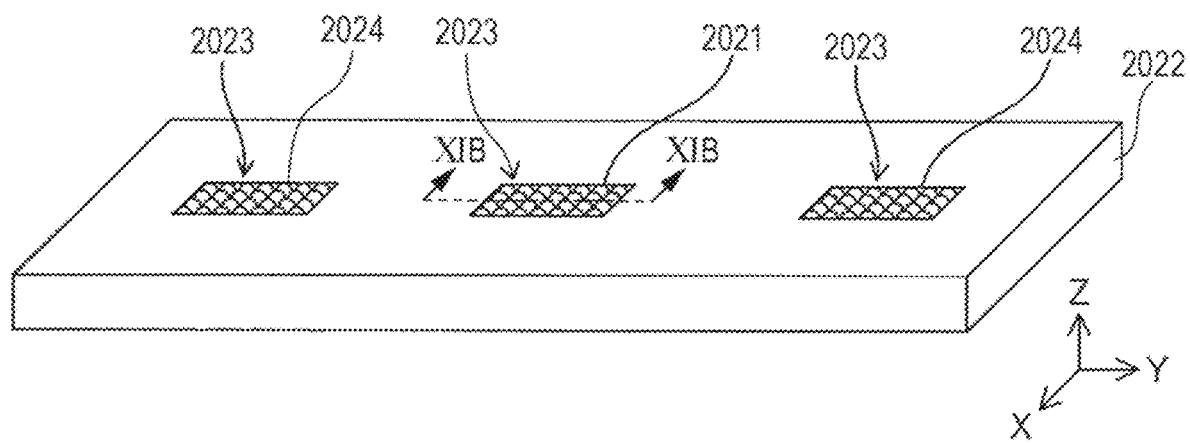
FIG. 11A is a perspective view illustrating an exemplary base material of Embodiment 1.

FIG. 11A is a perspective view illustrating an exemplary base material 2022 of Embodiment 1. The base material 2022 enhances light emitted from the complex 2032 (see FIG. 1) by plasmon resonance that occurs on the surface of the base material 2022. The base material 2022 is a substrate having a metal fine structure 2024 on the surface of the base material 2022. The metal fine structure 2024 may be formed on the entire principal surface of the base material 2022 or may be formed on part of the principal surface of the base material 2022. As illustrated in FIGS. 10 and 11A, the base material 2022 has a detection region 2023. The detection region 2023 is a region for optically detecting a virus by utilizing surface plasmon. The metal fine structure 2024 is arranged in the detection region 2023. When the detection region 2023 is irradiated with excitation light from the irradiator 204, metal particles that constitute the metal fine structure 2024 are excited to allow surface plasmon to occur on the surface of a metal film of the metal fine structure 2024.

Here, although the base material 2022 is placed on the bottom surface of the channel 2021 of the holder 202 in FIG. 10, the base material 2022 may be integrated with the channel 2021.

The base material 2022 is formed from a resin, such as a polyolefin, and has a plurality of protrusions in the detection region 2023. Some of the protrusions are covered with the metal film to constitute the metal fine structure 2024. On the metal fine structure 2024, a second substance has been immobilized. The second substance is, for example, an antibody having the property of specifically binding to a virus and is thus a so-called immobilized antibody. The details of the metal fine structure 2024 will be described hereinafter by means of FIG. 11B.

The feeder 203 introduces a sample and the complex 2032 into the holder 202. Concretely, the feeder 203 feeds, in drops, a sample liquid 2031 containing the sample and the complex 2032 to the holder 202. Here, the complex 2032 (see FIG. 1) is an antibody labeled with the quantum dot 20321a (see FIG. 1) and is thus a so-called labeled antibody. The sample is a liquid that potentially contains a virus and is a trapping liquid discharged from the cyclone 104 in the present embodiment.

If the sample contains a virus, the virus bonds with the metal fine structure 2024 through the immobilized antibody. On this occasion, the virus also binds to the labeled antibody, which is the complex 2032. In other words, the immobilized antibody, the virus, and the complex as a labeled antibody are bonded with the metal fine structure 2024. When the metal fine structure 2024 in this state is irradiated with excitation light from the irradiator 204, fluorescence is emitted from the complex 2032, which bonds with the virus, and is enhanced by surface plasmon. Hereinafter, fluorescence enhanced by surface plasmon is referred to as surface-enhanced fluorescence.

The irradiator 204 irradiates the holder 202 with excitation light. As the irradiator 204, publicly known technology may be employed without any particular limitation. The irradiator 204 may be a laser, such as a semiconductor laser or a gas laser.

The beam splitter 205 separates surface-enhanced fluorescence generated in the detection region 2023 from excitation light emitted from the irradiator 204. Concretely, the beam splitter 205 allows excitation light from the irradiator 204 to pass through, and separates and guides surface-enhanced fluorescence generated in the detection region 2023 to the detector 207.

The lens 206 focuses excitation light from the irradiator 204 that has passed through the beam splitter 205 on the detection region 2023. As the lens 206, publicly known technology may be employed without any particular limitation.

The detector 207 outputs electrical signals corresponding to the number of viruses in a sample by dispersing surface-enhanced fluorescence guided by the beam splitter 205 and detecting light in a particular wavelength range. As the detector 207, publicly known technology may be employed without any particular limitation provided that light in a particular wavelength range can be detected by dispersing light. As the detector 207, for example, an echelle spectrograph or a Czerny-Turner spectrograph, which disperses light using a diffraction grating and an interference filter that transmits light in a particular wavelength range for dispersing light, may be employed. Further, the detector 207 may include a notch filter for removing excitation light from the irradiator 204 before introducing light into the detector 207 or a long-pass filter that can block excitation light from the irradiator 204 while transmitting surface-enhanced fluorescence generated in the detection region 2023. It is noted that the illustration of a device for dispersing light is omitted at the detector 207 for the sake of simplification.

Configuration of Controller

The controller 300 (see FIG. 9) controls the operation of the entire detection system 10. Concretely, the controller 300 controls the trapping device 100 and the detection device 200.

More concretely, the controller 300 controls the start of measurement, causes the suction unit 101 to start suction of ambient air, and causes the pump 103 to supply a trapping liquid from the trapping liquid tank 102 to the cyclone 104. This allows mixing of the trapping liquid with fine particles in the cyclone 104 to prepare a sample. Subsequently, the sample is supplied from the cyclone 104 to the detection device 200. Further, the controller 300 causes the irradiator 204 to emit light and causes the detector 207 to detect surface-enhanced fluorescence. Here, the controller 300 may supply a sample liquid 2031 formed by mixing the sample with the complex 2032 (see FIG. 1) to the detector 200.

Moreover, the controller 300 supplies the sample liquid 2031 of a predetermined volume to the detection device 200 by controlling each pump under preset conditions based on input parameters, for example. Further, the controller 300 may have a timekeeping function and generate and store information about the time required for each operation. Still further, the controller 300 may receive measured values from the detection device 200 and calculate changes in the concentration of an airborne virus over time on the basis of the measured values and time information.

The controller 300 is realized by one or more dedicated electronic circuits, for example. One or more dedicated electronic circuits may be integrated on one chip or may be formed separately on a plurality of chips. Further, the controller 300 may be realized, in place of one or more dedicated electronic circuits, by a general-purpose processor (not illustrated) and memory (not illustrated) that stores a software program or instructions. In this case, such a processor acts as the controller 300 when the software program or instructions are executed.

Configuration of Metal Fine Structure

Figure 11B:
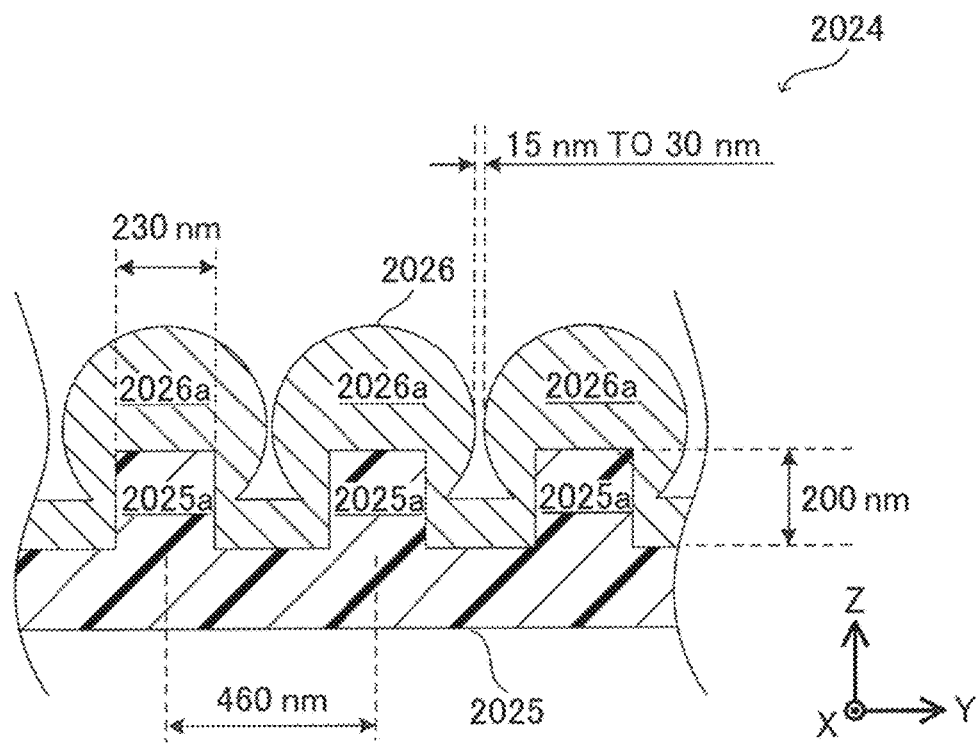
FIG. 11B is an enlarged cross-sectional view of a metal fine structure along the line XIB-XIB of FIG. 11A.

Now, the detailed configuration of the metal fine structure 2024 will be concretely described in reference to FIGS. 11A and 11B. FIG. 11B is an enlarged cross-sectional view of the metal fine structure 2024 along the line XIB-XIB of FIG. 11A.

As illustrated in FIG. 11A, the detection region 2023 of the base material 2022 is provided with the nanoscale metal fine structure 2024 for allowing surface plasmon to occur. In the present embodiment, the metal fine structure 2024 is a metal film-covered region in the detection region 2023 and includes a resin substrate 2025 and a metal film 2026.

The resin substrate 2025 has a nanostructure formed by nanoimprint or injection molding on either principal surface (surface on the positive side of the z-axis). As illustrated in FIG. 11B, the nanostructure includes a plurality of pillars 2025a. These pillars 2025a desirably have a ratio of the height to the pitch of 1:1 to 1:3. In the present embodiment, the wavelength of excitation light and the wavelength of fluorescence fall within 750 nm to 850 nm. Accordingly, the pillars 2025a desirably have a height of about 200 nm, a diameter of about 230 nm, and a pitch of about 460 nm, for example, in the present embodiment. Here, the nanostructure of the resin substrate 2025 is not limited to a plurality of pillars 2025a and may include a plurality of hemispheres instead.

The metal film 2026 is produced by film forming of a metal on the resin substrate 2025. In the metal film 2026, a plurality of protrusions 2026a are formed corresponding to a plurality of pillars 2025a of the resin substrate 2025. When the wavelength of excitation light and the wavelength of fluorescence fall within 750 nm to 850 nm, the thickness of the metal film 2026 is desirably about 400 nm. Moreover, the gap between the neighboring protrusions 2026a is desirably 100% to 200% of the sum of the length of an immobilized antibody, the length of a target substance, and the length of a labeled antibody.

The materials for the metal film 2026 need not be limited particularly and may be gold, silver, copper, aluminum, or an alloy containing any of these metals as a main component. Further, as the film forming method for the metal film 2026, electron beam (EB) deposition is employed, for example. Here, the film forming method for the metal film 2026 need not be limited particularly and may be sputtering or vacuum vapor deposition, for example.

Figure 12:
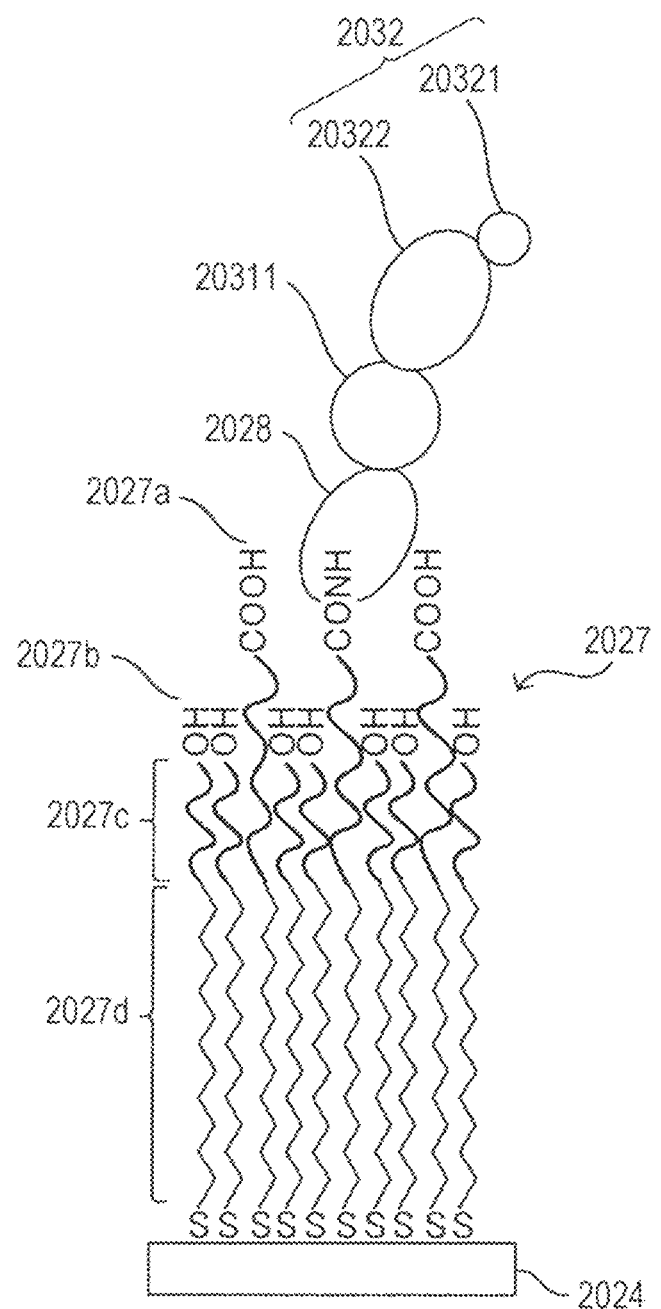
FIG. 12 illustrates a SAM of Embodiment 1.

On the metal film 2026, a self-assembled monolayer (hereinafter, referred to as SAM) is formed, and an antibody is immobilized (immobilized antibody) on the metal fine structure 2024 through the SAM. FIG. 12 illustrates a SAM 2027 of Embodiment 1.

As illustrated in FIG. 12, the SAM 2027 is formed on the metal fine structure 2024. The SAM 2027 includes linker molecules 2027a and non-linker molecules 2027b. An antibody is immobilized (immobilized antibody 2028) on the metal fine structure 2024 through the linker molecule 2027a of the SAM 2027.

The linker molecule 2027a has a thiol group at one end and a carboxy group at the other end. The thiol group bonds with the surface of the metal fine structure 2024, whereas the carboxy group forms a peptide bond with the antibody (immobilized antibody 2028).

Further, the linker molecule 2027a includes, between the thiol group and the carboxy group, an alkyl chain 2027c having 10 or more carbon atoms and a polyethylene glycol (PEG) chain. Concretely, the alkyl chain 2027c is connected to the thiol group and the polyethylene glycol chain 2027d, and the polyethylene glycol chain 2027d is connected to the alkyl chain 2027c and the carboxy group.

The non-linker molecule 2027b has a thiol group at one end and a hydroxy group at the other end. The thiol group bonds with the surface of the metal fine structure 2024, whereas the hydroxy group suppresses, due to the hydrophilicity, nonspecific adsorption of the labeled antibody 20322 and the surface-modified quantum dot 20321.

Further, the non-linker molecule 2027b includes, between the thiol group and the hydroxy group, an alkyl chain 2027c having 10 or more carbon atoms and a polyethylene glycol chain 2027d. Concretely, the alkyl chain 2027c is connected to the thiol group and the polyethylene glycol chain 2027d, and the polyethylene glycol chain 2027d is connected to the alkyl chain 2027c and the hydroxy group.

When a virus (target substance) 20311 is contained in the sample liquid 2031, the virus 20311 binds to the immobilized antibody 2028 on the metal fine structure 2024. The virus 20311 also binds to the labeled antibody 20322, which has been labeled with the surface-modified quantum dot 20321.

When the metal fine structure 2024 in this state is irradiated with excitation light, fluorescence is emitted from the complex 2032 and is enhanced by surface plasmon that occurs on the metal fine structure 2024. In other words, surface-enhanced fluorescence corresponding to the number of viruses is emitted.

Here, both the immobilized antibody 2028 and the labeled antibody 20322 are antibodies having the property of specifically binding to a target substance and may be a VHH antibody or IgG antibody, for example.

Operation of Detection Device

Figure 13:
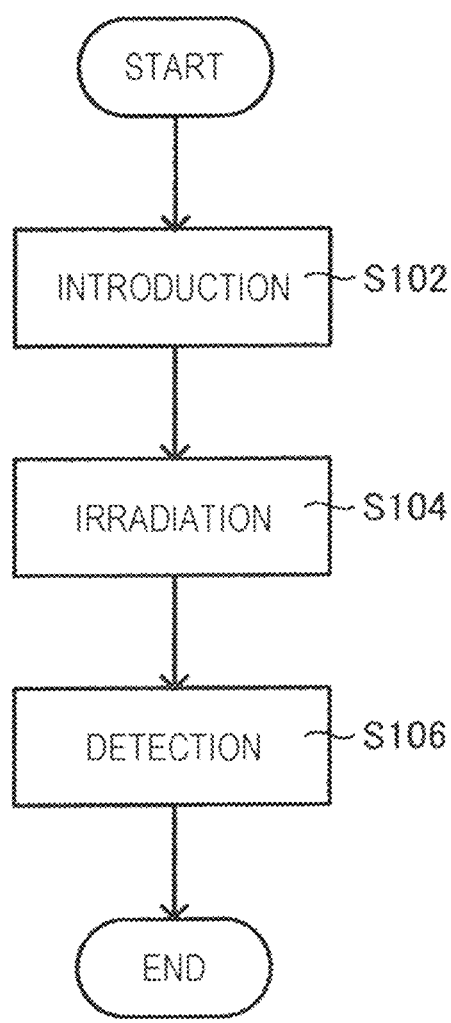
FIG. 13 is a flow chart of the exemplary operation of the detection device according to Embodiment 1.

The operation of the detection device 200 configured as in the foregoing will be described in reference to FIGS. 10 and 13. FIG. 13 is a flow chart of the exemplary operation of the detection device 200 according to Embodiment 1.

First, the feeder 203 introduces the sample liquid 2031 containing a complex and a sample that potentially contains a virus into the holder 202 (S102). Subsequently, the irradiator 204 irradiates the holder 202, into which the sample liquid 2031 has been introduced, with excitation light (S104). After that, the detector 207 measures surface-enhanced fluorescence, which is fluorescence emitted from the complex upon irradiation with excitation light and enhanced by surface plasmon, thereby detecting a virus in the sample liquid 2031 (S106).

Effects and so Forth

As in the foregoing, the complex 2032 according to Embodiment 1 is a complex containing: a first substance having a property of specifically binding to a target substance; a quantum dot that contains silicon as a main component and that is negatively charged on a surface; and a linker substance that contains a compound represented by general formula (1) below and that covers the surface of the quantum dot, where the first substance has been immobilized on the surface of the quantum dot through the linker substance:

$$X\text{—}L\text{—}Si\text{—}(R_1)(R_2)(OR_3) \tag{1}$$

where X is a basic functional group; $R_1$, $R_2$, and $R_3$ are each independently an alkyl group; and L is an alkylene group.

As described above, since the linker substance contains a compound having a basic functional group and has one silanol group within the molecule, quantum dots do not bond with each other through the linker substance even when the surface of the quantum dots are covered with the linker substance containing the compound represented by general formula (1) above. In other words, the linker substance represented by general formula (1) above having only one silanol group within the molecule cannot bond with other quantum dots after bonding with one quantum dot. For this reason, even when the surface of quantum dots is covered with the linker substance containing the compound represented by general formula (1) above, the quantum dots are less likely to aggregate. Consequently, the complex according to Embodiment 1 exhibits satisfactory dispersibility. Herein, a basic functional group is, for example, a proton-withdrawing functional group and an electron-donating functional group. In other words, a basic functional group is a positively charged functional group when ionized. Further, the quantum dots formed from an inorganic material exhibit higher light resistance than organic fluorescent substances. For this reason, the quantum dots are less susceptible to photobleaching. Accordingly, the complex of Embodiment 1 has stable luminescence characteristics. In addition, silicon as a main component of the quantum dots has extremely low adverse effects on the human body and the environment. Accordingly, the complex of Embodiment 1 can reduce adverse effects on the human body and the environment, Further, silicon accounts for about 28% of the Earth's crust and is the second most abundant element after oxygen. For this reason, by incorporating silicon as a main component into quantum dots, the complex according to an aspect of the present disclosure not only contributes to environmental conservation (sustainability) into the future but also can realize lower costs.

In the complex 2032 according to Embodiment 1, for example, X in general formula (1) above is an amino group.

By having such a structure, the linker substance exhibits high bonding properties with the first substance, for example, when the first substance has a carboxy group at the terminal. For this reason, it is possible to satisfactorily bond a quantum dot with the first substance through the linker substance. Consequently, the stability of the complex according to Embodiment 1 is enhanced.

In the complex 2032 according to Embodiment 1, for example, $R_1$ and $R_2$ is a methyl group, $R_3$ is an ethyl group, and L is a propylene group in general formula (1) above.

As described above, since the linker substance has only one silanol group within the molecule, quantum dots are less likely to aggregate even if the linker substance has a basic functional group, in other words, has a functional group to be cationized. For this reason, the complex according to Embodiment 1 maintains satisfactory dispersibility.

In the complex 2032 according to Embodiment 1, for example, the surface of the quantum dot contains boron and phosphorus.

By having such constitution, the quantum dot is negatively charged. For this reason, the complex according to Embodiment 1 exhibits satisfactory dispersibility.

Further, the detection device 200 according to Embodiment 1 detects, using any of the above-described complexes, a target substance by labeling the target substance.

As in the foregoing, quantum dots are less susceptible to photobleaching. For this reason, a complex containing such a quantum dot as a constituent maintains stable luminescence characteristics even when irradiated with high-intensity light. Accordingly, by labeling the target substance with the complex, the detection device according to Embodiment 1 can detect a low concentration of the target substance at high sensitivity. Moreover, the complex maintains stable luminescence characteristics even under continuously irradiation with light. For this reason, the detection device according to Embodiment 1 can detect the target substance by calculating or summing changes in the target substance over time. Accordingly, by using any of the above-described complexes, the detection device according to Embodiment 1 enables highly reliable detection. Further, quantum dots have a larger Stokes shift than conventional organic fluorescent dyes. For this reason, when quantum dots are used as a fluorescent substance, it is possible to pass fluorescence alone through an optical filter while blocking excitation light. Accordingly, by using any of the above-described complexes, the detection device according to Embodiment 1 can detect a low concentration of target substance at high accuracy.

The detection device 200 according to Embodiment 1 includes, for example, a holder for holding a base material on which a second substance having a property of specifically binding to the target substance has been immobilized; a feeder for introducing the complex and a sample that potentially contains the target substance into the holder; an irradiator for irradiating the holder with excitation light; and a detector for detecting the target substance on the basis of light emitted from the complex due to the excitation light with which the holder is irradiated.

By the above configuration, a sandwich structure in which the second substance immobilized on the base material, the target substance, and the first substance in the complex are bonded in this order is formed in the holder. Accordingly, the detection device according to Embodiment 1 can detect a low concentration of the target substance at high sensitivity by detecting light emitted from the complex in the sandwich structure.

In the detection device 200 according to Embodiment 1, for example, the base material enhances light emitted from the complex by plasmon resonance that occurs on the surface of the base material.

Consequently, the detection device according to Embodiment 1 can detect a low concentration of target substance at high sensitivity.

In the detection device 200 according to Embodiment 1, for example, the base material is a substrate having a metal fine structure on the surface of the base material.

Consequently, since localized plasmon occurs on the surface of the substrate, light emitted from the complex is enhanced by plasmon resonance. For this reason, the detection device according to Embodiment 1 can detect a low concentration of target substance at high sensitivity.

Embodiment 2

Next, the detection device according to Embodiment 2 will be described in reference to the drawings.

Detection Device

Figure 14:
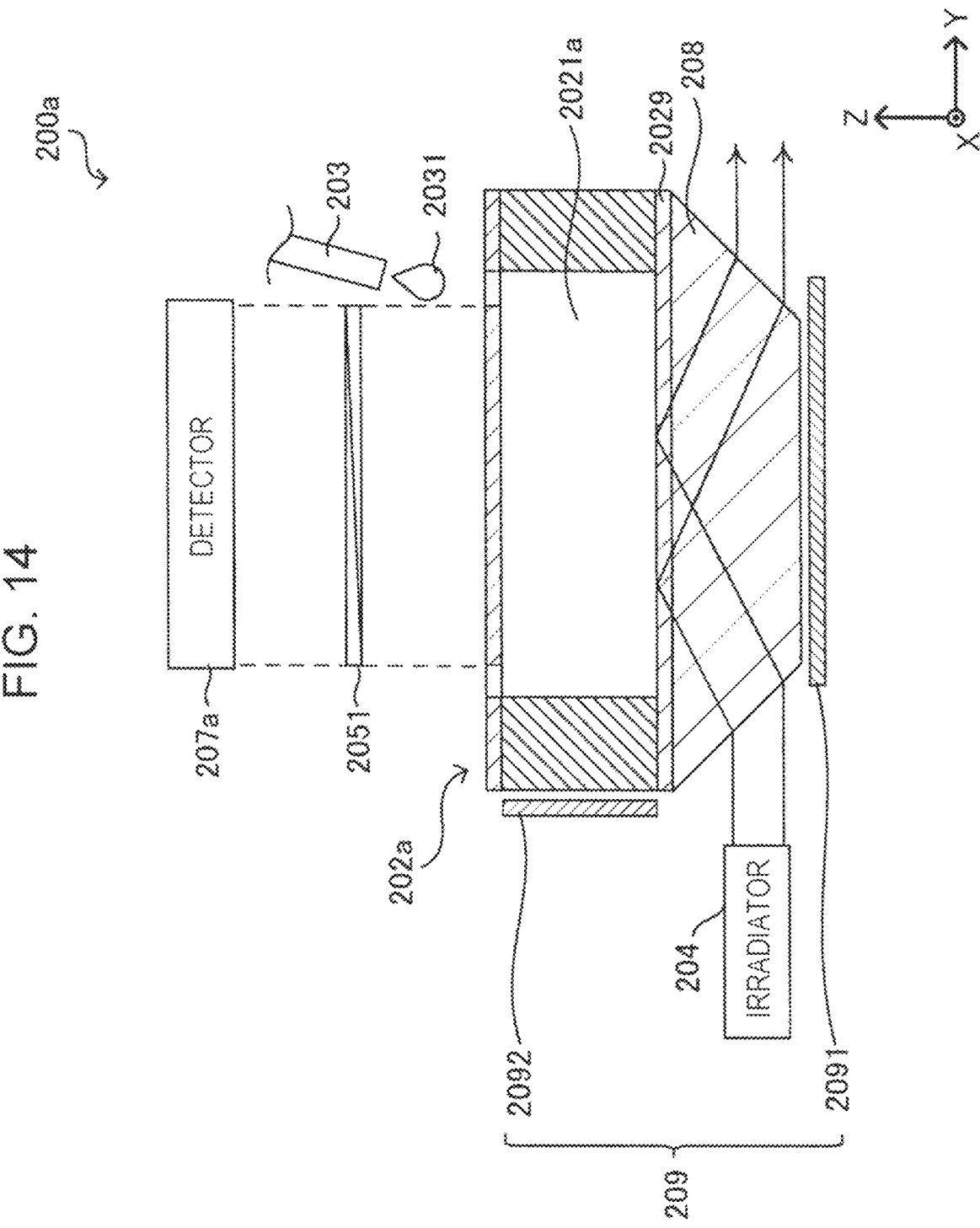
FIG. 14 schematically illustrates an exemplary detection device according to Embodiment 2.

FIG. 14 schematically illustrates an exemplary detection device 200a according to Embodiment 2. In FIG. 14, the same components as those in FIG. 10 are denoted by the same signs and the repetitive explanations thereof will be omitted.

The detection device 200 according to Embodiment 1 is described as an example in which the base material 2022 is a substrate having the metal fine structure 2024 on the surface. Meanwhile, base materials (not illustrated) are fine particles exhibiting magnetism (hereinafter, also referred to as magnetic fine particles) in the detection device 200a according to Embodiment 2. Such magnetic fine particles are ferromagnets.

Moreover, Embodiment 1 is described as an example in which light emitted from the complex 2032 is enhanced by plasmon resonance that occurs on the surface of the metal fine structure 2024. Meanwhile, in Embodiment 2, the detection device 200a further includes an applicator 209 and the magnetic fine particles configured to move in a predetermined direction in response to a magnetic field generated by the applicator 209. Hereinafter, aspects different from Embodiment 1 will be mainly described.

As illustrated in FIG. 14, the detection device 200a according to Embodiment 2 includes a holder 202a, a feeder 203, an irradiator 204, a long-pass filter 2051, a detector 207a, and an applicator 209.

The holder 202a includes a channel 2021a, a refractive index modulation layer 2029, and a glass substrate 208. The holder 202a holds magnetic fine particles on which an antibody having the property of specifically binding to a virus has been immobilized (hereinafter, referred to as antibody-attached magnetic fine particles).

The channel 2021a has a feed port for supplying a sample liquid 2031 into the channel 2021a and a discharge port for discharging the sample liquid 2031 in the channel 2021a outside the holder 202a. The channel 2021a is partitioned with walls disposed on the principal surface (hereinafter, referred to as top surface) of the refractive index modulation layer 2029 on the positive side of the z-axis. The walls are formed of silicon rubber, for example. By forming the walls with silicone rubber, a liquid in the channel 2021a is less likely to leak outside the channel 2021a.

The refractive index modulation layer 2029 may comprise a single layer or two or more layers having different refractive indexes provided that particular-wavelength light of the incident light on the refractive index modulation layer 2029 can be enhanced through interference (hereinafter, referred to as resonance) within the layer. In the case of the refractive index modulation layer 2029 comprising a plurality of layers, for example, when the incident light on the refractive index modulation layer 2029 undergoes total reflection at the interface between the refractive index modulation layer 2029 and the channel 2021a, part of the incident light propagates while undergoing multilayer reflection within the refractive index modulation layer 2029. Consequently, the particular-wavelength light is enhanced by resonance within the refractive index modulation layer 2029. For this reason, the intensity of near-field light that occurs on the surface of the refractive index modulation layer 2029 (hereinafter, referred to as top surface of the refractive index modulation layer 2029) on the side of the channel 2021a. Here, the near-field light is non-propagating light that occurs on the rear surface (here, the top surface of the refractive index modulation layer 2029) of the reflection surface for total reflection of the incident light and is evanescent light, for example. The non-propagating near-field light exists only in the vicinity of the top surface of the refractive index modulation layer 2029 and decays with distance from the top surface. Herein, the region in which near-field light exists is referred to as near-field.

The glass substrate 208 is disposed in contact with the refractive index modulation layer 2029. The glass substrate 208 refracts incident light at a predetermined refractive index. The glass substrate 208 is a prism, for example. The glass substrate 208 and the refractive index modulation layer 2029 constitute an optical waveguide. As illustrated in FIG. 14, light emitted from the irradiator 204 enters the glass substrate 208 from the incident surface of the optical waveguide (glass substrate 208 surface on the negative side of the y-axis), propagates within the refractive index modulation layer 2029, and exits from the emission surface of the optical waveguide (glass substrate 208 surface on the positive side of the y-axis) outside the glass substrate 208.

The feeder 203 introduces the sample liquid 2031 into the holder 202a. A sample and the complex 2032 in the sample liquid 2031 are bonded with an antibody-attached magnetic fine particle to form a sandwich structure in which a virus is sandwiched between the complex 2032 and the antibody-attached magnetic fine particle. Here, the feeder 203 may introduce a mixture of the sample liquid 2031 and antibody-attached magnetic fine particles into the holder 202a.

The applicator 209 includes a first applicator 2091 and a second applicator 2092. The first applicator 2091 is a magnet, for example, and disposed on the negative side of the z-axis (hereinafter, referred to as lower side) of the waveguide. The first applicator 2091 generates a first magnetic field that attracts magnetic fine particles toward the refractive index modulation layer 2029 (i.e., downward). The first applicator 2091 attracts, by generating the first magnetic field, magnetic fine particles and sandwich structures to the top surface of the refractive index modulation layer 2029. For example, the first applicator 2091 adjusts the intensity of the first magnetic field such that magnetic fine particles and sandwich structures are present within the near-field (hereinafter, also referred to as within near-field illumination region). Consequently, the complexes 2032 in the sandwich structures are excited within the near-field to emit light. The second applicator 2092 is a magnet, for example, and disposed on the negative side of the y-axis (hereinafter, referred to as lateral direction) of the channel 2021a. The second applicator 2092 generates a second magnetic field that sweeps magnetic fine particles in a predetermined direction (here, the negative side of the y-axis). Consequently, magnetic fine particles and sandwich structures are swept in the predetermined direction. Here, the intensity of the first magnetic field and the second magnetic field may be regulated by adjusting the distance between the first applicator 2091 and the channel 2021a and the distance between the second applicator 2092 and the channel 2021a, respectively, or by controlling the voltage applied to the first applicator 2091 and the second applicator 2092, respectively.

The irradiator 204 irradiates the holder 202a with excitation light. In the present embodiment, the irradiator 204 irradiates the glass substrate 208 with excitation light. Since the irradiator 204 is the same as the irradiator of Embodiment 1, the explanation thereof is omitted here.

Herein, Embodiment 2 is described as an example in which the near-field is formed on the top surface of the waveguide (i.e., the top surface of the refractive index modulation layer 2029) by total reflection of excitation light within the waveguide and the quantum dot 20321a in the complex 2032 is excited within the near-field. Embodiment 2, however, is not limited to such an example. For example, excitation light emitted from the irradiator 204 may be converted into a light sheet, and quantum dots may be excited with the light sheet. Further, quantum dots may be excited by plasmon resonance.

The long-pass filter 2051 blocks excitation light from the irradiator 204 and allows light emitted from the complex (here, fluorescence) to pass through.

The detector 207a receives fluorescence that has passed through the long-pass filter 2051 and forms a two-dimensional image. In the present embodiment, the detector 207a forms a two-dimensional image by receiving fluorescence emitted from the complex in the sandwich structure that has been swept within the near-field. On the two-dimensional image, fluorescence emitted from individual complexes is shown as light spots. The detector 207a detects only sandwich structures that are swept in a predetermined direction as light spots that move in the predetermined direction. Accordingly, the detection device 200a according to Embodiment 2 can measure the concentration of a virus in a sample by detecting the virus as moving spots (moving light spots) and counting the moving spots.

Operation of Detection Device

Figure 15:
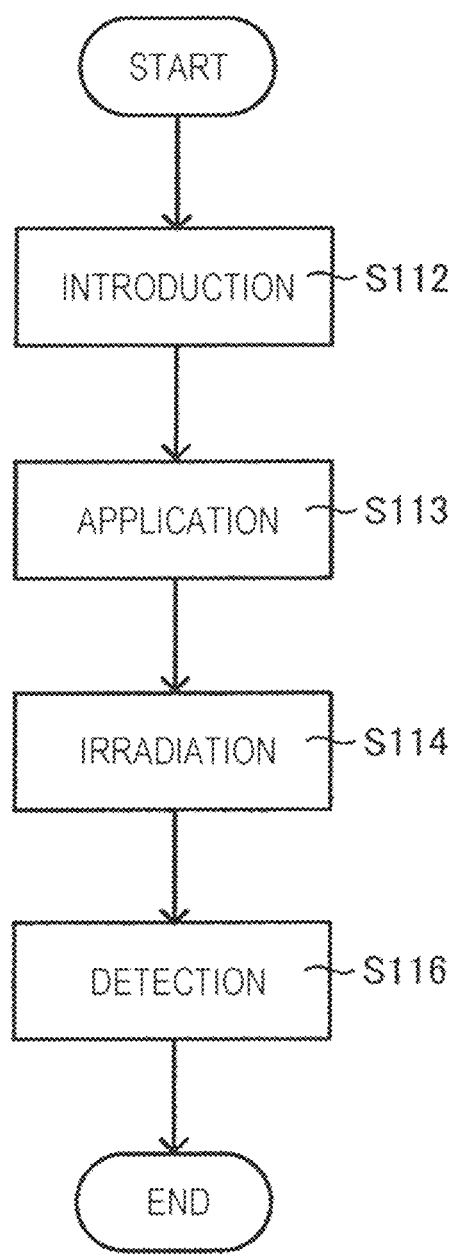
FIG. 15 is a flow chart of the exemplary operation of the detection device according to Embodiment 2.

The operation of the detection device 200a configured as in the foregoing will be described in reference to FIG. 15. FIG. 15 is a flow chart of the exemplary operation of the detection device 200a according to Embodiment 2.

As illustrated in FIG. 10, Embodiment 1 is described as an example in which the base material 2022 is a substrate having the metal fine structure 2024 (see FIG. 11B) on the surface and is held within the holder 202. Meanwhile, base materials (not illustrated) are magnetic fine particles in Embodiment 2. Accordingly, different from Embodiment 1, the detection device 200a may further add antibody-attached magnetic fine particles when the sample liquid 2031 is prepared by mixing complexes with a sample that potentially contains a virus. Hereinafter, the exemplary operation of the detection device 200a in which the feeder 203 introduces a mixture of the sample liquid 2031 and antibody-attached magnetic fine particles into the holder 202a will be described.

First, the preparation of the mixture will be described. The detection device 200a mixes a sample that potentially contains a virus with a solution prepared in advance by mixing complexes with antibody-attached magnetic fine particles in a mixing section (not illustrated). Consequently, a mixture of the sample, the complexes, and the antibody-attached magnetic fine particles is prepared. In the mixture, an antibody immobilized on the magnetic fine particle, the virus (antigen), and an antibody immobilized on the surface of a quantum dot are bonded in this order through antigen-antibody reactions to form a sandwich structure.

As shown in FIG. 15, the feeder 203 introduces the above-described mixture into the holder 202a (S112).

Subsequently, the applicator 209 generates magnetic fields in the holder 202a (S113). The applicator 209 includes the first applicator 2091 for generating a first magnetic field within the holder 202a and the second applicator 2092 for generating a second magnetic field within the holder 202a. The first applicator 2091 generates the first magnetic field within the holder 202a to attract sandwich structures and magnetic fine particles in the mixture that has been introduced into the holder 202a to the vicinity of the interface between the channel 2021a and the refractive index modulation layer 2029. Subsequently, the second applicator 2092 generates the second magnetic field within the holder 202a to sweep the sandwich structures and the magnetic fine particles in a predetermined direction (the negative side of the y-axis shown in FIG. 14, for example). As described above, in step S113, the sandwich structures and the magnetic fine particles are moved in a predetermined direction along the interface by generating magnetic fields in the holder 202a.

Next, the irradiator 204 irradiates the glass substrate 208 of the holder 202a with excitation light, thereby irradiating the holder 202a, into which the mixture has been introduced, with excitation light (S114). The glass substrate 208 is a prism, for example, and refracts light within the glass substrate 208 at a predetermined refractive index. In the present embodiment, the refractive index modulation layer 2029 is disposed on the principal surface of the glass substrate 208 on the channel 2021a side. Only particular-wavelength light of the incident light on the glass substrate 208 is enhanced through resonance at the interface between the refractive index modulation layer 2029 and the channel 2021a.

Subsequently, the detector 207a detects a virus in the mixture by measuring fluorescence emitted from the complexes upon irradiation with excitation light (S116). The detector 207a receives fluorescence emitted from the complexes in the sandwich structures and forms a two-dimensional image. As in the foregoing, in step S113, the sandwich structures and the magnetic fine particles are attracted to the vicinity of the interface between the channel 2021a and the refractive index modulation layer 2029 by the first magnetic field generated by the first applicator 2091. In this step, the complexes in the sandwich structures receive excitation light in the vicinity of the interface and emit fluorescence. The detector 207a receives the fluorescence and forms a two-dimensional image. On this occasion, fluorescence emitted from each sandwich structure is shown as a light spot on the two-dimensional image. After that, in step S113, the sandwich structures and the magnetic fine particles attracted to the vicinity of the interface are swept in a predetermined direction (the negative direction of the y-axis of FIG. 14, for example) along the interface by the second magnetic field. On this occasion, the detector 207a detects only the sandwich structures swept in the predetermined direction as light spots moving in the predetermined direction. As in the foregoing, the detector 207a can measure the concentration of an airborne virus by detecting light emitted from the complexes in the sandwich structures as moving spots (light spots) and counting the moving spots.

Effects and so Forth

As in the foregoing, the detection device according to Embodiment 2 further includes an applicator for generating a magnetic field in the holder, where the base materials are magnetic fine particles and thus move in a predetermined direction in response to a magnetic field generated by the applicator.

By the above constitution, sandwich structures, in each of which a first substance in the complex, a target substance, and a second substance immobilized on the surface of the base material are bonded in this order, move in a predetermined direction within the holder in response to a magnetic field generated by the applicator. On this occasion, when the holder is irradiated with excitation light, the complexes in the sandwich structures emit fluorescence. Consequently, according to the detection device of Embodiment 2, the sandwich structures moving in a predetermined direction can be detected as the movement of light spots. Moreover, quantum dots in the complexes are formed from an inorganic material and are thus less susceptible to photobleaching. For this reason, the quantum dots maintain stable luminescence characteristics while the sandwich structures move in a predetermined direction in response to a magnetic field even under continuous irradiation with excitation light. Consequently, the detection device of Embodiment 2 can detect a low concentration of target substance at high accuracy.

Other Embodiments

As in the foregoing, the detection device and the detection method according to one or a plurality of aspects of the present disclosure are described on the basis of embodiments. However, the present disclosure is not limited to these embodiments. The scope of one or a plurality of aspects of the present disclosure may encompass, without departing from the spirit of the present disclosure, embodiments with various modifications conceivable to those skilled in the art and embodiments of combined constituents of different embodiments.

Herein, Embodiment 2 is described as an example in which the detection device 200a (see FIG. 14) includes a waveguide formed from the glass substrate 208 and the refractive index modulation layer 2029, where the near-field is formed in the vicinity of the top surface of the refractive index modulation layer 2029. However, the detection device may include a metal thin film of gold, silver, or the like on the top surface of the refractive index modulation layer 2029. Consequently, localized surface plasmon occurs on the metal thin film, and fluorescence emitted from the complexes in the sandwich structures is thus further enhanced by plasmon resonance.

Moreover, Embodiment 2 is described as an example in which the sandwich structures are attracted to the refractive index modulation layer 2029 by the first magnetic field generated by the first applicator 2091 and light emitted from the complexes in the sandwich structures is enhanced within the near-field. However, moreover, localized surface plasmon may occur on the surface of the magnetic fine particles. Consequently, fluorescence emitted from the complexes in the sandwich structures is further enhanced by plasmon resonance.

Further, Embodiment 2 is described as an example in which a waveguide is provided below the holder 202a to form the near-field on the bottom surface of the channel 2021a (in other words, the top surface of the refractive index modulation layer 2029), thereby enhancing light emitted from the complexes. However, the detection device need not include a waveguide. For example, in the detection device, the channel 2021a may be irradiated with excitation light almost horizontally from the side of the channel 2021a (the y-axis direction in FIG. 14). By such irradiation with excitation light, it is possible to irradiate the entire channel 2021a with light and to prevent excitation light from directly entering the detector 207a. In this case, localized surface plasmon occurs on the surface of the magnetic fine particles. Consequently, fluorescence emitted from the complexes in the sandwich structures is enhanced by plasmon resonance.

Still further, Embodiment 2 is described as an example in which the base materials are magnetic fine particles and the sandwich structures moving in a predetermined direction in response to a magnetic field generated by the applicator 209 are detected as the movement of light spots. However, the detection device need not include the applicator 209. The detection device may be a flow cytometer, for example. In this case, localized surface plasmon occurs on the surface of the magnetic fine particles. Consequently, fluorescence emitted from complexes in the sandwich structures is enhanced by plasmon resonance. Meanwhile, fluorescence emitted from free complexes, which are away from the magnetic fine particles, is neither affected by plasmon resonance nor enhanced.

As in the foregoing, since fluorescence emitted from the complexes in the sandwich structures is enhanced by plasmon resonance, the detection device can detect a low concentration of target substance at high sensitivity and high accuracy.

Further, the complex according to the present disclosure is less susceptible to photodegradation, such as photobleaching, even under continuous irradiation with excitation light. For this reason, by using the complex according to the present disclosure, it is possible to realize in a detection device not only higher sensitivity and higher accuracy but also faster detection. This reduces time and costs for detection, thereby enhancing efficiency.

The complex and the detection device using the complex according to the present disclosure are applicable to a detection system that plays a gatekeeping role at a room entrance and detects the concentration of an airborne virus in the room highly sensitively to reduce the risk of viral infection for those who are staying in the room.

What is claimed is:

1. A complex comprising:
   a first substance having a property of specifically binding to a target substance;
   a quantum dot that contains silicon as a main component and that is negatively charged on a surface; and
   a linker substance that contains a compound represented by general formula (1) below and that covers the surface of the quantum dot,
   wherein:
   the first substance has been immobilized on the surface of the quantum dot through the linker substance:

$$X\text{—}L\text{—}Si\text{—}(R_1)(R_2)(OR_3) \quad (1)$$

where
   X is a basic functional group
   $R_1$, $R_2$, and $R_3$ are each independently an alkyl group, and
   L is an alkylene group, and
   the linker substance has one silanol group bonding to the silicon quantum dot and the first substance bonds to the linker substance through the basic functional group.

2. The complex according to claim 1, wherein X is an amino group.

3. The complex according to claim 2, wherein
   $R_1$ and $R_2$ are a methyl group,
   $R_3$ is an ethyl group, and
   L is a propylene group.

4. The complex according to claim 1, wherein the surface of the quantum dot contains boron and phosphorus.

* * * * *